United States Patent
Song

(10) Patent No.: US 9,243,235 B2
(45) Date of Patent: *Jan. 26, 2016

(54) METHOD OF PRODUCING RECOMBINANT PROTEINS WITH MANNOSE-TERMINATED N-GLYCANS

(71) Applicant: Agency for Science, Technology and Research, Singapore (SG)

(72) Inventor: Zhiwei Song, Singapore (SG)

(73) Assignee: Agency for Science, Technology and Research, Singapore (SG)

(*) Notice: Subject to any disclaimer, the term of this patent is extended or adjusted under 35 U.S.C. 154(b) by 0 days.

This patent is subject to a terminal disclaimer.

(21) Appl. No.: 14/620,856

(22) Filed: Feb. 12, 2015

(65) Prior Publication Data

US 2015/0152402 A1 Jun. 4, 2015

Related U.S. Application Data

(62) Division of application No. 13/636,952, filed as application No. PCT/SG2011/000118 on Mar. 24, 2011.

(60) Provisional application No. 61/317,369, filed on Mar. 25, 2010.

(51) Int. Cl.
| | |
|---|---|
| *C12P 21/06* | (2006.01) |
| *C12N 9/24* | (2006.01) |
| *C12N 15/00* | (2006.01) |
| *C12N 9/42* | (2006.01) |
| *C12P 21/00* | (2006.01) |

(52) U.S. Cl.
CPC ............ *C12N 9/2445* (2013.01); *C12N 9/2402* (2013.01); *C12P 21/005* (2013.01); *C12Y 204/01101* (2013.01); *C12Y 302/01045* (2013.01)

(58) Field of Classification Search
CPC .......... C12P 21/005; C12N 9/24; C12N 15/00
USPC ................................. 435/183, 69.1; 514/12.1
See application file for complete search history.

(56) References Cited

U.S. PATENT DOCUMENTS

2013/0129755 A1  5/2013  Song

FOREIGN PATENT DOCUMENTS

WO   WO-2010/033085   3/2010

OTHER PUBLICATIONS

Charbonneau et al., Role of carbohydrate structures in CEA-mediated intercellular adhesion, Cell Adhesion and Communication, 1999, 7(3): 233-244.
Goh et al., RCA-I-resistant CHO mutant cells have dysfunctional GnT I and expression of normal GnT I in these mutants enhances sialylation of recombinant erythropietin, Metabolic Engineering, 2010, 12: 360-368.
International Search Report and Written Opinion for PCT/SG2011/000118, dated Jul. 4, 2011, 16 pages.
Otto et al., Sialylated Complex-type N-glycans enhance the signaling activity of soluble inercellular adhesion molecule-1 in mouse astrocytes, The Journal of Biological Chemistry, 2004, 279(34): 35201-35209.
Schurpf et al., Consequences of soluble ICAM-1 N-glycan alterations on receptor binding and signaling kinetics in mouse astrocytes, Open Glycoscience, 2008, 1: 40-51.
Van Patten et al., Effect of Mannose Chain Length on Targeting of Glucocerebrosidase for Enzyme Replacement Therapy of Gaucher Disease, Glycobiology, 2007, 17(5): 467-478.
Zhou et al., N-Glycans of ADAMTS13 modulate its secretion and von Willebrand factor cleaving activity, Blood, 2009, 113(4): 929-935.

*Primary Examiner* — Maryam Monshipouri
(74) *Attorney, Agent, or Firm* — Choate, Hall & Stewart LLP; Charles E. Lyon; Nishat A. Shaikh

(57) ABSTRACT

We describe a method of expressing a recombinant protein comprising mannose-terminated N-glycans from a host cell, the method comprising: (a) introducing a nucleic acid encoding a recombinant protein into a Chinese Hamster Ovary (CHO) cell comprising a mutation in the GnT 1 gene (GenBank Accession Number AF343963) leading to loss of GnT 1 function; and (c) expressing the recombinant protein from the host cell, in which the expressed recombinant protein comprises a mannose-terminated glycan structure, and in which the method does not include a step of introducing functional GnT-I into the host cell. The method may be used for producing recombinant glucocerebrosidase with a mannose-terminated glycan structure, suitable for treatment or prevention of Gaucher's Disease.

25 Claims, 9 Drawing Sheets

METHOD OF PRODUCING RECOMBINANT PROTEINS WITH MANNOSE-TERMINATED N-GLYCANS

This application is a divisional of U.S. patent application Ser. No. 13/636,952, filed Oct. 19, 2012, now U.S. Pat. No. 9,175,278, issued Nov. 3, 2015, which is a U.S. National Stage of International Application No. PCT/SG2011/000118, filed Mar. 24, 2011, which claims the benefit of U.S. Provisional Application No. 61/317,369, filed Mar. 25, 2010, the entire content of each of which is hereby incorporated herein by reference.

The foregoing applications, and each document cited or referenced in each of the present and foregoing applications, including during the prosecution of each of the foregoing applications ("application and article cited documents"), and any manufacturer's instructions or catalogues for any products cited or mentioned in each of the foregoing applications and articles and in any of the application and article cited documents, are hereby incorporated herein by reference. Furthermore, all documents cited in this text, and all documents cited or reference in documents cited in this text, and any manufacturer's instructions or catalogues for any products cited or mentioned in this text or in any document hereby incorporated into this text, are hereby incorporated herein by reference. Documents incorporated by reference into this text or any teachings therein may be used in the practice of this invention. Documents incorporated by reference into this text are not admitted to be prior art.

FIELD

This invention relates to the fields of biotechnology, molecular biology and medicine. The invention in particular relates to a Chinese Hamster Ovary cell line and its use in expression of recombinant proteins which have mannose-terminated N-glycans for targeting the protein to dendritic cells and macrophages, including glucocerebrosidase for the treatment of Gaucher disease, anti-cancer vaccines such as human mucin 1 (MUC1), HER2/neu and carcinoembryonic antigen (CEA) and anti-viral vaccines.

SEQUENCE LISTING

In accordance with 37 CFR §1.52 (e(5), a Sequence Listing in the form of a text file (entitled "Sequence Listing_ST25.txt," created on Feb. 11, 2015, and 13 kilobytes in size) is incorporated herein by reference in its entirety.

BACKGROUND

Gaucher's disease is an autosomal recessive lysosomal storage disease which results from a deficiency in the lysosomal enzyme, glucocerebrosidase. This causes the accumulation of glucoceramide within peripheral macrophages, resulting in cellular enlargments. Gaucher's disease causes spleen, liver and bone marrow to malfunction and deteriorate.

Ceredase is the commercial name for glucocerebrosidase derived from human placenta. The intravenous infusion of Ceredase was shown to be clinically useful and has been approved for the treatment of Gaucher's disease in a study published in 1991 (Proc. Natl. Acad. Sci. 1990, 1913-1916). In order for the enzyme to be taken up by the target cell type, the enzyme is first deglycosylated, resulting in a mannose-terminated glycan structure so that it is taken up into the macrophage via its lectin receptors. This placental derived glucocerebrosidase treatment was approved by the Federal Drug Administration in April, 1991. However, due to the anticipated demand for this new replacement enzyme therapy, ways to produce this protein through means of recombinant expression have been sought.

Cerezyme is a recombinant form of glucocerebrosidase produced in CHO cells. The expressed protein is treated with exoglucosidases to produce the mannose sugars on the terminus of the existing polysaccharide chain, leading to a selective uptake of the enzyme by macrophages that are present in liver, spleen and skeleton. The drug works as well as the naturally occurring protein does by catalyzing the hydrolysis of the glycolipid glucocerebroside to glucose and ceramide as part of the normal degradation pathway for membrane lipids. However, the method of production of Cerezyme involves extensive treatment with exoglucosidases to trim the glycan structures to terminal mannose structures. This process is difficult to control and adds to the cost of production.

Major antigen presenting cells, such as dendritic cells and macrophages, express mannose-biding C-type lectins on their surface. Recombinant glycoproteins with mannose-terminated N-glycans are capable of specifically binding to and targeting such dendritic cells and macrophages via the mannose-binding C-type lectin on macrophages. Accordingly, it is desired for recombinant proteins which are intended for use as vaccines to comprise mannose-terminated N-glycans. The same problems as described above for production of Cerezyme exist in relation to methods of production of other recombinant glycoproteins with mannose-terminated N-glycans for use, e.g., in vaccines.

There therefore exists a need in the art for a method of production of glucocerebrosidase and other recombinant glycoproteins with mannose-terminated N-glycans which avoids such post-expression processing.

One possibility is to make use of CHO cells which have mutations in the post-translational glycosylation pathway. Van Patten et al. (2007, Glycobiology, 17, 467-478) describes a study carried out to examine the use of alternative expression systems to produce Cerezyme (recombinant glucocerebrosidase) that would circumvent the need to use exoglucosidases to trim the glycan structures to terminal mannose structures. The alternative expression systems tested included non-mammalian expression systems, CHO cells cultured in kifunensine and a CHO glycosylation mutant, Lec 1.

The study showed that these different expression systems could indeed produce glucocerebrosidase containing terminal mannose residues. Glucocerebrosidase produced by Lec 1 cells was in particular found to function just as well as the commercially available Cerezyme. However, the study also identified a number of significant issues with each alternative.

With regard to use of Lec 1 cells, Van Patten et al. (2007, Glycobiology, 17, 467-478) found that both this expression system was characterised by low productivity. Given this, it would be difficult, if not impossible, to scale up expression to industrial production levels.

Furthermore, Lec 1 cells are not amenable to large scale culture. Lec 1 cells were originally isolated from a proline auxotroph for genetic studies and do not survive very well in normal large scale cell culture conditions or in chemically defined media and cultured in suspension. Furthermore, the media has to supplemented with proline and even then the cells die easily. Thus this cell line is not robust and therefore not suitable for use in the production of recombinant proteins as their expected growth characteristics and productivity is inferior to existing industrial cell lines.

There therefore exists a need in the art for a scalable method of production of glucocerebrosidase and other recombinant glycoproteins with mannose-terminated N-glycans that avoid that avoids these problems of the prior art.

SUMMARY

According to a 1$^{st}$ aspect of the present invention, we provide a method of expressing a recombinant protein comprising mannose-terminated N-glycans from a host cell, the method comprising: (a) introducing a nucleic acid encoding a recombinant protein into a Chinese Hamster Ovary (CHO) cell comprising a mutation in the GnT 1 gene (GenBank Accession Number AF343963) leading to loss of GnT 1 function; and (c) expressing the recombinant protein from the host cell, in which the expressed recombinant protein comprises a mannose-terminated glycan structure.

The method may be such that it does not include a step of introducing functional GnT-I into the host cell.

The method may be such that it does not include a step of introducing a nucleic acid encoding functional GnT-I into the host cell.

The CHO cell may be selected with *Ricinus communis* agglutinin I (RCA-I) or a descendent thereof. The CHO cell selected with RCA-I or descendent thereof may comprise a mutation in the GnT-I gene.

The method may be such that selection with RCA-I comprises comprising culturing CHO cells in the presence of *Ricinus communis* agglutinin I (RCA-I) and selecting cells which survive the culture, in which for example: (a) the CHO cells are exposed to RCA-I at a concentration of between 0.1 µg/ml to 100 µg/ml, for example up to 50 µg/ml or up to 20 µg/ml, such as 10 µg/ml or 5 µg/ml; or (b) the CHO cells are exposed RCA-I for a period of from an hour, a few hours (such as 2, 3, 4, 5, 6, 7, 8, 9, 10, 11, 12), overnight, to a few days, such as 2 days or 3 days, such as overnight, optionally together with a further step of selecting cells which do not react with RCA-I in an agglutination test.

The host cell may be adapted to suspension culture.

The host cell may comprise a JW152 cell line (deposited at ATCC under the Budapest Treaty as accession number PTA-9657).

The method may be such that at step (b) an expression construct comprising nucleic acid encoding the recombinant protein in an expression vector such as pcDNA3.1 is introduced into the host cell.

The nucleic acid encoding the recombinant protein may be transformed or stably integrated into the host cell.

The method may be such that it further comprises the step of isolating and/or purifying the expressed recombinant protein.

The protein may comprise (a) a sequence having GenBank Accession Number NP_000148.2 or a variant, homologue, derivative or fragment thereof having glucocerebrosidase activity; (b) a tumour-specific or tumour-associated antigen such as MUC1, HER2/neu and carcinoembryonic antigen (CEA) and antigenic portions thereof; or (c) a viral antigen.

The nucleic acid may comprise a sequence having GenBank Accession Number NM_000157 or a variant, homologue, derivative or fragment thereof encoding a protein comprising glucocerebrosidase activity.

There is provided, according to a 2$^{nd}$ aspect of the present invention, a mannose-terminated recombinant protein such as glucocerebrosidase, MUC1, HER2/neu or carcinoembryonic antigen (CEA) expressed by a host cell line according to the 1$^{st}$ aspect of the invention.

We provide, according to a 3$^{rd}$ aspect of the present invention, a JW152 cell (deposited at ATCC under the Budapest Treaty as accession number PTA-9657) comprising a nucleic acid sequence encoding a protein with glucocerebrosidase activity, glucocerebrosidase, MUC1, HER2/neu or carcinoembryonic antigen (CEA) and which is preferably capable of expression of such a protein.

As a 4$^{th}$ aspect of the present invention, there is provided a method of expressing a mannose-terminated protein having glucocerebrosidase activity from a host cell, glucocerebrosidase, MUC1, HER2/neu or carcinoembryonic antigen (CEA), the method comprising: (a) providing a JW152 cell (deposited at ATCC under the Budapest Treaty as accession number PTA-9657) comprising a nucleic acid encoding a protein having glucocerebrosidase activity, glucocerebrosidase, MUC1, HER2/neu or carcinoembryonic antigen (CEA); and (b) allowing the relevant protein to be expressed from the cell.

We provide, according to a 5$^{th}$ aspect of the present invention, a method comprising expressing a mannose-terminated recombinant protein from a host cell as set out above, or providing a mannose-terminated recombinant protein as set out above, and administering the mannose-terminated recombinant protein to an individual in need thereof.

The method may be for treatment of Gaucher's Disease, in which the mannose-terminated recombinant protein comprises a mannose-terminated recombinant protein with glucocerebrosidase activity.

The present invention, in a 6$^{th}$ aspect, provides a mannose-terminated recombinant protein according to Claim 12 for use in a method of treatment of Gaucher's Disease, in which the mannose-terminated recombinant protein comprises a mannose-terminated recombinant protein with glucocerebrosidase activity.

In a 7$^{th}$ aspect of the present invention, there is provided a JW152 cell (deposited at ATCC under the Budapest Treaty as accession number PTA-9657) comprising a nucleic acid sequence encoding a protein, which protein when expressed is desired to comprise a mannose-terminated glycan structure.

The practice of the present invention will employ, unless otherwise indicated, conventional techniques of chemistry, molecular biology, microbiology, recombinant DNA and immunology, which are within the capabilities of a person of ordinary skill in the art. Such techniques are explained in the literature. See, for example, J. Sambrook, E. F. Fritsch, and T. Maniatis, 1989, *Molecular Cloning: A Laboratory Manual*, Second Edition, Books 1-3, Cold Spring Harbor Laboratory Press; Ausubel, F. M. et al. (1995 and periodic supplements; *Current Protocols in Molecular Biology*, ch. 9, 13, and 16, John Wiley & Sons, New York, N.Y.); B. Roe, J. Crabtree, and A. Kahn, 1996, *DNA Isolation and Sequencing: Essential Techniques*, John Wiley & Sons; J. M. Polak and James O'D. McGee, 1990, In Situ *Hybridization: Principles and Practice*; Oxford University Press; M. J. Gait (Editor), 1984, *Oligonucleotide Synthesis: A Practical Approach*, Irl Press; D. M. J. Lilley and J. E. Dahlberg, 1992, *Methods of Enzymology: DNA Structure Part A: Synthesis and Physical Analysis of DNA* Methods in Enzymology, Academic Press; Using Antibodies: A Laboratory Manual: Portable Protocol NO. I by Edward Harlow, David Lane, Ed Harlow (1999, Cold Spring Harbor Laboratory Press, ISBN 0-87969-544-7); Antibodies: A Laboratory Manual by Ed Harlow (Editor), David Lane (Editor) (1988, Cold Spring Harbor Laboratory Press, ISBN 0-87969-314-2), 1855. Handbook of Drug Screening, edited by Ramakrishna Seethala, Prabhavathi B. Fernandes (2001, New York, N.Y., Marcel Dekker, ISBN 0-8247-0562-9); and Lab Ref: A Handbook of Recipes, Reagents, and Other Reference Tools for Use at the Bench, Edited Jane Roskams and Linda Rodgers, 2002, Cold Spring Harbor Laboratory, ISBN 0-87969-630-3. Each of these general texts is herein incorporated by reference.

SEQUENCE LISTING

Figure 1:
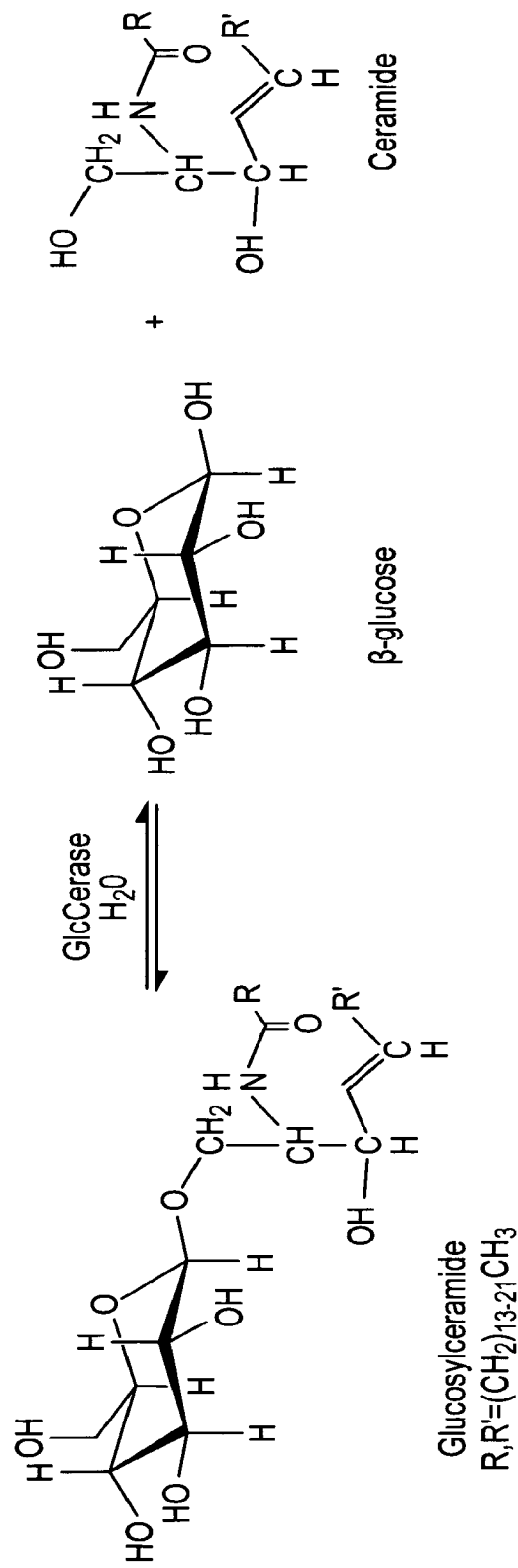
FIG. 1 is a drawing showing the pathway by which glucosylceramide is hydrolysed by glucocerebrosidase into β-glucose and ceramide.
Figure 2:
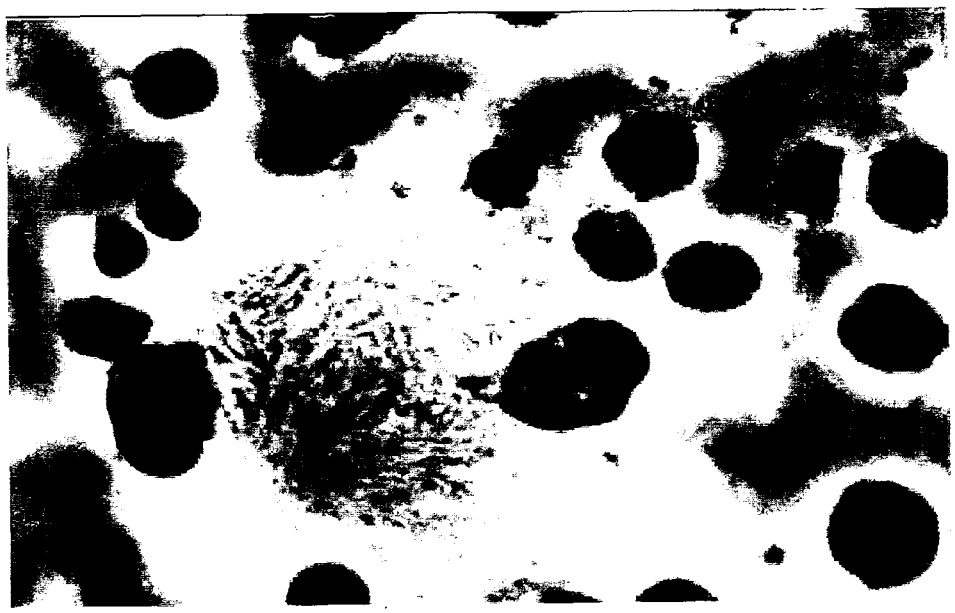
FIG. 2 is micrograph showing cells of a Gaucher patient, including enlarged macrophages containing undigested glucocerebroside (from www.nlm.nih.gov/medlineplus/ency/imagepages/1450.htm).
Figure 3:
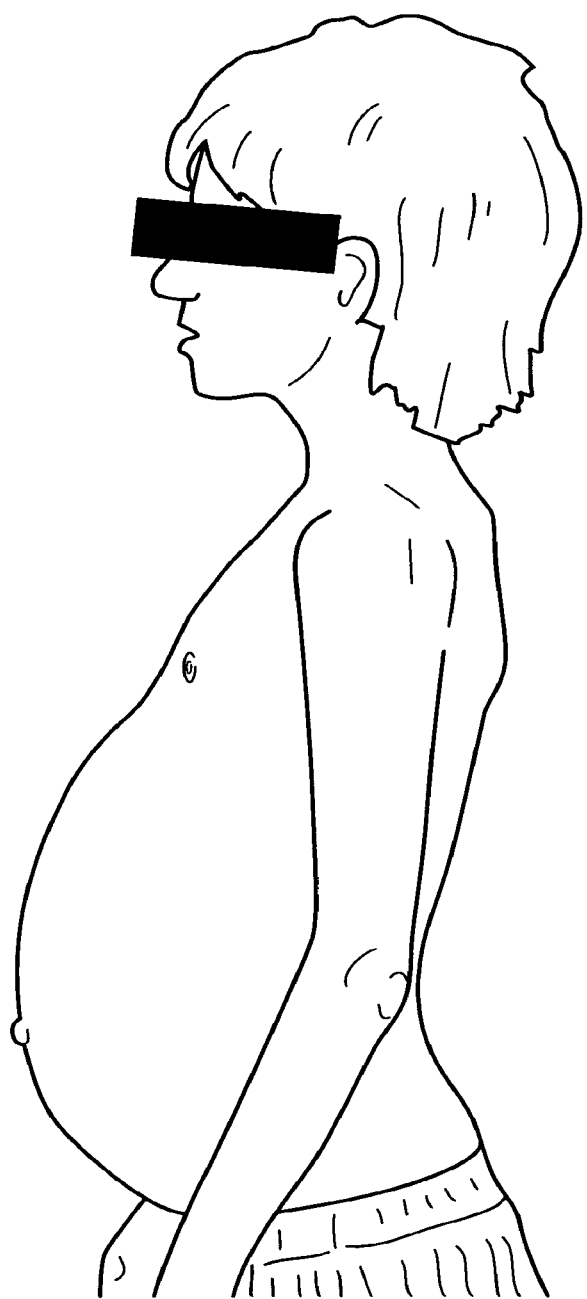
FIG. 3 is a drawing showing a patient with Gaucher's disease (from geneticpeople.com/?p=276).
Figure 4:
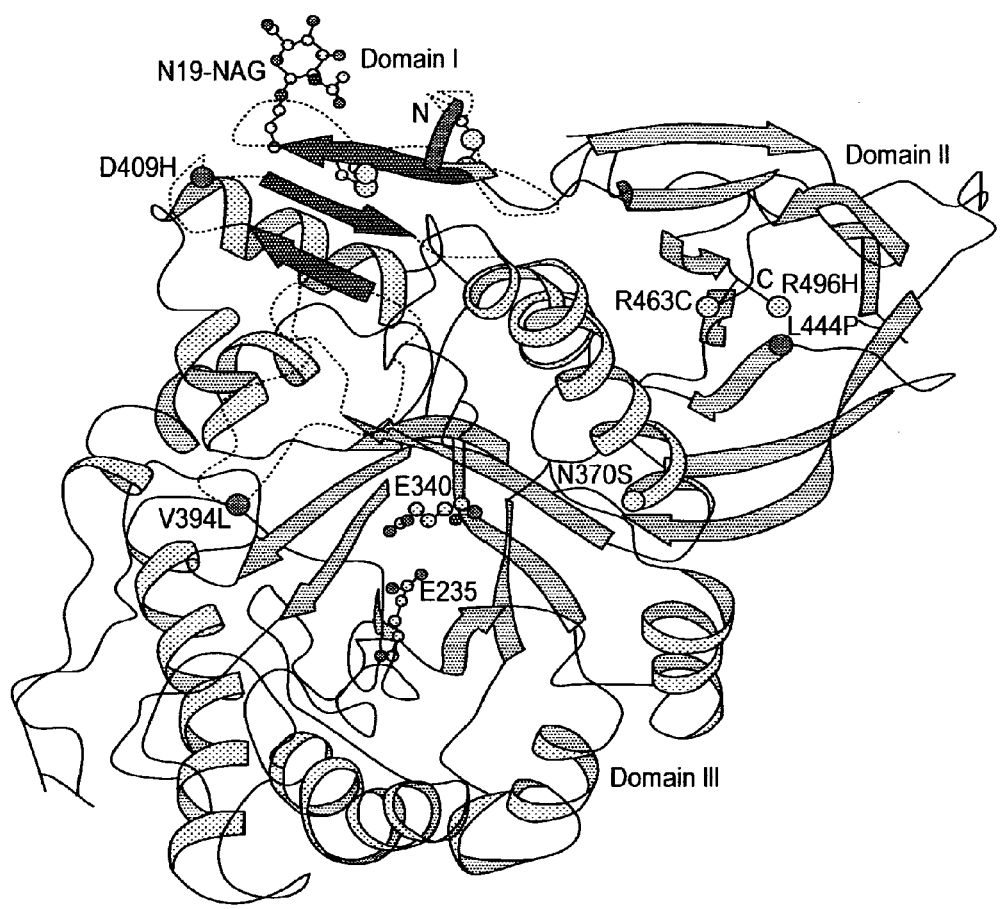
FIG. 4 is a drawing showing the structure of glucocerebrosidase. Glucocerebrosidase contains a single N-linked glycan attached to N-19. EMBO reports, 2003, 4:704.
Figure 5:
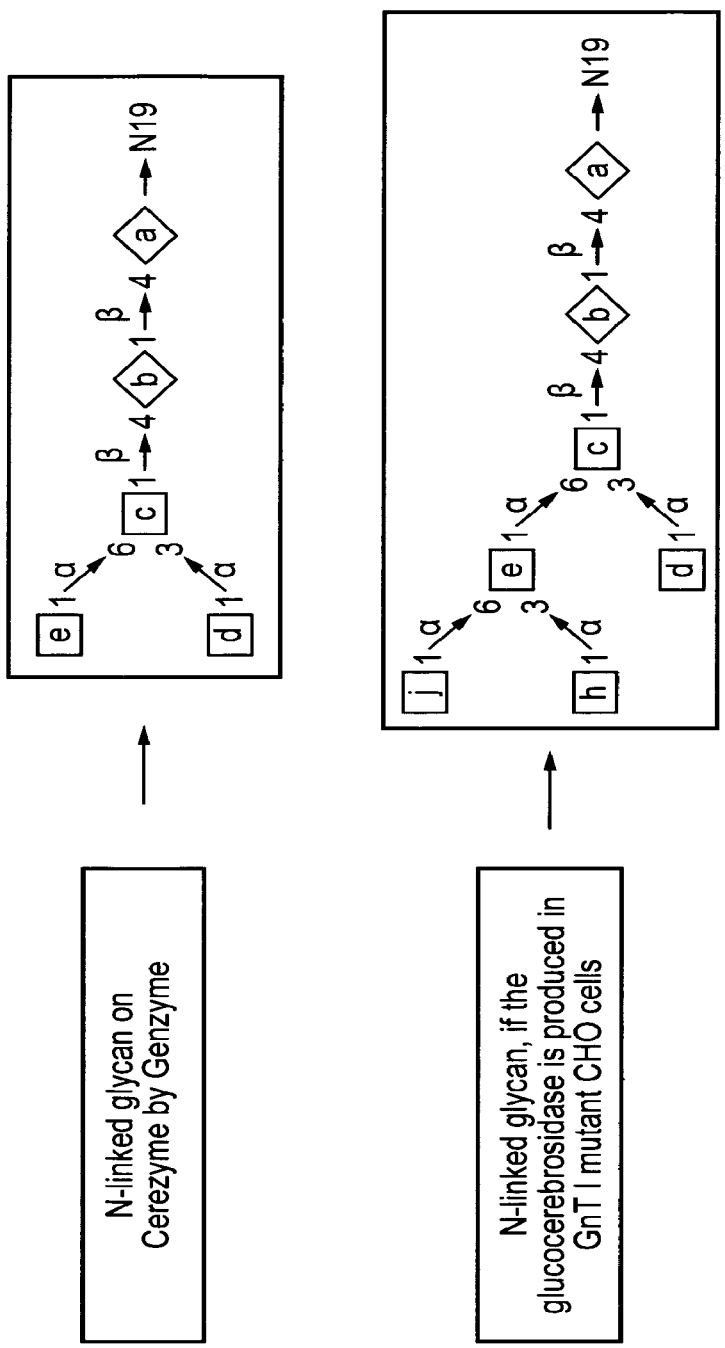
FIG. 5 is a drawing showing that terminal mannose residues direct Cerezyme to target cells. Similarly, terminal mannose residues direct glucocerebrosidase is produced in GnT I mutant CHO cells to target cells.
Figure 6:
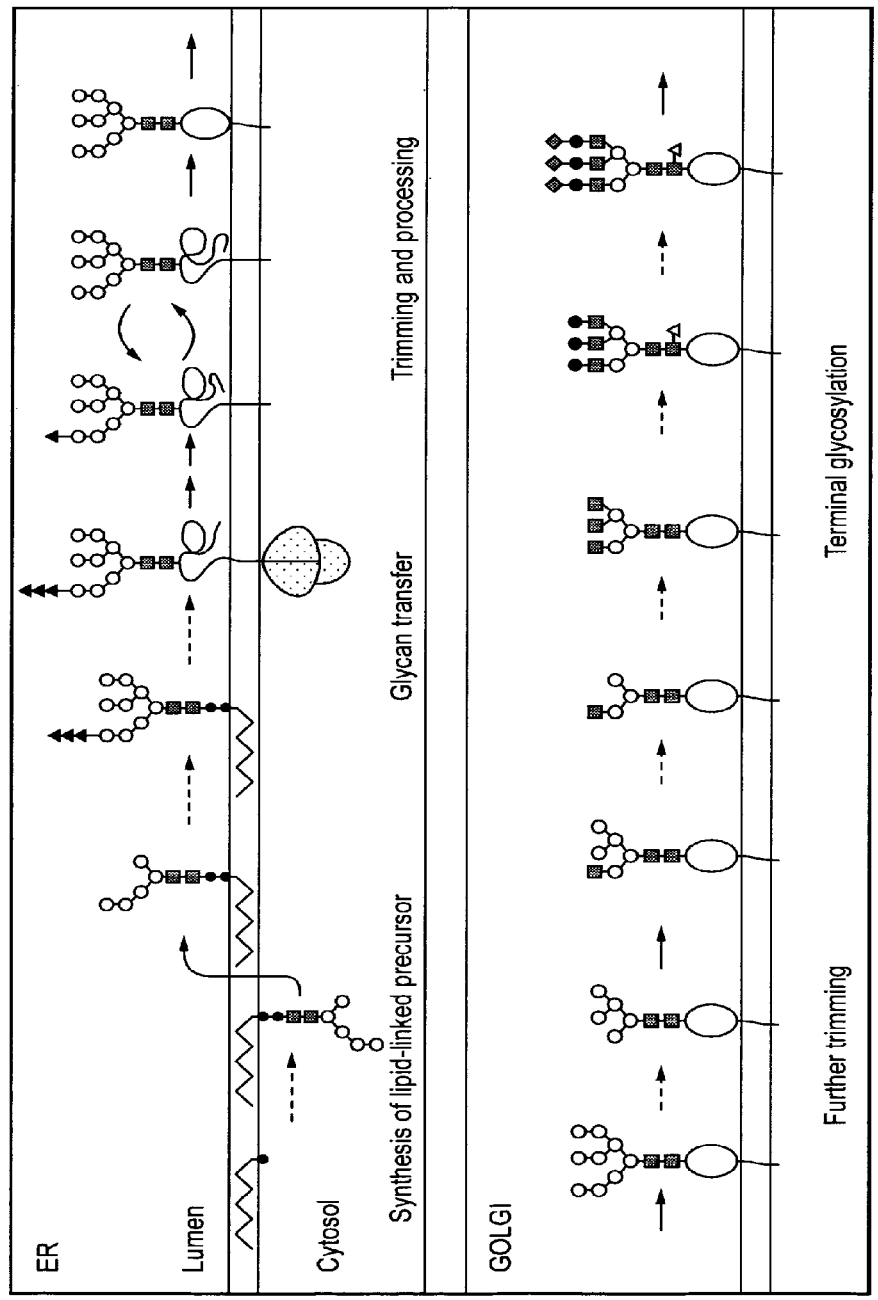
FIG. 6 is a drawings showing protein N-Glycosylation in the ER and Golgi of mammalian cells. Helenius & Aebi, Science, 2001, 291:2364.

SEQ ID NO: 1 is a nucleic acid sequence of a N-acetylglucoaminyltransferase I cDNA from CHO JW152 cells. SEQ ID NO: 2 is an amino acid sequence of N-acetylglucoaminyltransferase I encoded by SEQ ID NO: 1.

DETAILED DESCRIPTION

Using a cytotoxic lectin, RCA-I, we have isolated a number of CHO mutant cell lines, including JW152, from CHO-K1 cells. Several of these stably transfected lines have been adapted to suspension culture and grown in serum-free medium.

We demonstrate that recombinant proteins of interest, such as glucocerebrosidase, produced by such cells, including JW152 cells, that are stably transfected with relevant expressing cDNAs comprise mannose-terminated glycan structures. These results suggest that JW152 and other cells have the potential to become a host cell line for producing proteins, such as mannose-terminated recombinant proteins (by which we mean recombinant proteins comprising mannose-terminated N-glycans) including glycoprotein drugs and vaccines.

This is beneficial for expression of polypeptides which are to be targeted to cells with lectin receptors, for example, macrophages. As described in detail in this document, GnT-I deficient cells made according to the methods described here may be used for the production of recombinant glucocerebrosidase and other proteins of interest, which has mannose-terminated glycan structures and is hence able to be taken up by macrophages.

We therefore provide for a method of expressing a recombinant protein from a host cell. The recombinant protein may comprise glucocerebrocidase, a viral antigen or a tumour antigen. The method comprises providing a host cell comprising a Chinese Hamster Ovary (CHO) cell which is selected with *Ricinus communis* agglutinin I (RCA-I) or a descendent thereof. The host cell may comprise JW152. The method may comprise introducing a nucleic acid encoding a recombinant protein into the host cell. Alternatively, or in addition, the host cell may already comprise such a nucleic acid, prior to the process of selection. The nucleic acid may be integrated into the genome of the host cell.

The method may further comprise the step of expressing the recombinant protein from the host cell. The expressed recombinant protein may comprise a mannose-terminated glycan structure. The method may be such that it does not include a step of introducing functional GnT-I into the host cell.

Using such a method, the expressed recombinant protein may comprise one or more N-glycan structures. We demonstrate that N-glycans produced in these cells comprise mainly mannose-terminated structures. This is in contrast to the normal complex-type N-glycans that also contain sialic acid and galactose residues using expression from other cells.

Accordingly, we provide for the treatment or prevention of diseases such as Gaucher's Disease, by such expression and administration of mannose-terminated recombinant glucocerebrosidase, from such CHO host cells.

We also provide for the treatment or prevention of diseases, by such expression and administration of mannose-terminated recombinant proteins of interest, from such CHO host cells.

Such diseases include cancer, which according to the methods and compositions described here may be treated or prevented by expression and administration of mannose-terminated recombinant tumour-specific or tumour-associated antigens, from such CHO host cells. For example, anti-cancer vaccines may be made from MUC1, HER2/neu and carcinoembryonic antigen (CEA)—or antigenic portions thereof—expressed according to the methods and compositions described here.

Examples of other tumour-specific and tumour-associated antigens are provided in further detail below.

Further diseases include viral associated or caused diseases, which according to the methods and compositions described here may be treated or prevented by expression and administration of mannose-terminated recombinant viral antigens, from such CHO host cells. Examples of viral antigens are provided in further detail below.

In relation to Gaucher's Disease, mannose-terminated recombinant glucocerebrosidase protein for the treatment of disorders such as Gaucher's Disease may be administered by intravenous infusion over 1-2 hours. Dosage should be individualized to each patient. Initial dosages may range from about 2.5 U/kg of body weight 3 times a week to 60 U/kg once every 2 weeks.

Disease severity may dictate that treatment be initiated at a relatively high dose or relatively frequent administration. Dosage adjustments should be made on an individual basis and may increase or decrease, based on achievement of therapeutic goals as assessed by routine comprehensive evaluations of the patient's clinical manifestations.

For the purposes of the above paragraphs, an enzyme unit (U) is defined as the amount of enzyme that catalyzes the hydrolysis of 1 micromole of the synthetic substrate para-nitrophenyl-β-D-glucopyranoside (pNP-Glc) per minute at 37° C.

Use of such GnT-I deficient CHO cells as host cells has a number of advantages. First, as the recombinant expressed proteins of interest have mannose-terminated glycan structures, there is no need for enzymatic treatment to expose these. Second, the GnT-I deficient CHO host cells are derived from a parental CHO-K1 cell line that is very robust and are accordingly suited for recombinant expression in industrial applications.

For example, JW152 cells originated from CHO-K1 cells grow very well under bioprocess conditions. Such JW152 cells have also been adapted to chemically defined medium and cultured in suspension.

The cell line JW152 was deposited on 11 Dec. 2008 at the American Type Culture Collection, 10801 University Boulevard, Manassas, Va. 20110-2209, United States of America under the accession number PTA-9657 as the International Deposition Number under the Budapest Treaty on the International Recognition of the Deposit of Microorganisms for the Purposes of Patent Procedure.

We therefore provide for a Chinese Hamster Ovary (CHO) cell or cell line which is capable of higher expression of mannose-terminated protein compared to a wild type Chinese Hamster Ovary cell, and the use of such a host cell or cell line for expression of mannose-terminated recombinant proteins.

The CHO cell capable of higher expression of mannose-terminated protein may be produced by a suitable selection method such as a RCA-1 selection method. Such a method is described in further detail in "CHO Cells and Cell Lines" below. Therefore, RCA-I can be used to isolate CHO glycosylation mutant cells that produce higher amounts of mannose-terminated recombinant proteins.

Such a selection method is therefore specifically included in the methods and compositions described here.

We therefore provide for the use of a Chinese Hamster Ovary (CHO) cell or cell line which is capable of higher expression of mannose-terminated protein compared to a wild type Chinese Hamster Ovary cell, the CHO cell being obtainable by selection with *Ricinus communis* agglutinin I (RCA-I), in the expression of mannose-terminated recombinant proteins. In general, we provide a RCA-I resistant CHO cell or cell line, such as an RCA-I resistant CHO-K1 cell or cell line, for such a use.

Genetic analysis has revealed a dysfunctional N-Acetylglucosaminyltransferase I (GnT I) gene in JW152 cells. Molecular cloning of the GnT I cDNA from the mutant cells identified a point mutation that results in a premature stop codon. As a result, the JW152 cells can only synthesize a truncated version of GnT I protein with only 338 amino acids, rather than the normal protein which contains 447 amino acids.

Using RCA-I we have isolated many more CHO mutant lines (about 100 clones). Genetic analyses showed that they all lack functional GnT I gene. Many of them carry a different point mutation in the coding region of GnT I gene, suggesting that they derived from different original clones. Each of these may be used for expression of mannose-terminated recombinant proteins. The mutations in the GnT I genes from these further CHO cell lines are shown in Table E1 below.

Accordingly, we provide for a Chinese Hamster Ovary (CHO) cell which is capable of higher expression of mannose-terminated protein compared to a wild type Chinese Hamster Ovary cell, the CHO cell comprising a mutation in the GnT I gene. We further provide for a Chinese Hamster Ovary (CHO) cell or cell line which is capable of higher expression of mannose-terminated protein compared to a wild type Chinese Hamster Ovary cell, the CHO cell being obtainable by selection with *Ricinus communis* agglutinin I (RCA-I) and comprising a mutation in the GnT I gene. We provide for the use of such a cell or cell line as a host cell for expression of recombinant proteins, such as mannose-terminated recombinant proteins The mutation in the GnT I gene may comprise any point mutation, deletion, inversion, etc. The mutation in the GnT I gene may encode a partially functioning, or non-functioning GnT I polypeptide. The mutation in the GnT I gene may encode a truncated GnT I polypeptide.

We provide for CHO cells and cell lines comprising each of these mutant CHO cell lines and clones. We provide for specific cell lines derived from RCA-I selection and capable of higher expression of mannose-terminated protein compared to wild type or native CHO cells or parental cells. We provide for the use of such cells, host cells and cell lines for expression of mannose-terminated recombinant proteins.

We provide for mutant CHO nucleic acid and polypeptide sequences comprised in such cells or cell lines, as described in further detail below.

The CHO cell or cell line may comprise a JW152 cell line. It may comprise a JW80 cell line. It may comprise a JW36 cell line. It may comprise a KFC15002 cell line. It may comprise a KFC15071 cell line. It may comprise a KFC5008 cell line. It may comprise a JW152 cell line. It may comprise a KFC5026 cell line. It may comprise a KFC20011 cell line. It may comprise a KFC15047 cell line.

The CHO cell or cell line may be transfected with a nucleic acid encoding a protein of interest, for example a heterologous or recombinant protein. Such a protein might comprise a glycoprotein. In particular, such a protein might comprise a protein of interest such as a protein with glucocerebrosidase activity, a tumour-specific or tumour associated antigen or a viral antigen, as described in further detail below.

As noted above, we provide for the nucleic acid themselves, e.g., a nucleic acid encoding a mutant GnT I gene, or a fragment, variant, derivative or homologue of such a nucleic acid. The nucleic acid encoding a mutant GnT I gene, fragment, variant, derivative or homologue may cause a CHO cell comprising it to be capable of higher expression of mannose-terminated protein, compared to a CHO cell which does not comprise such a nucleic acid, for example a wild type CHO cell. The nucleic acid encoding the mutant GnT I gene may comprise a sequence shown as SEQ ID NO: 1 or a variant, homologue, derivative or fragment thereof.

GnT-I mutants made according to the methods described here show high levels of sialylation, as described in PCT/SG2009/000348 (published as) in the presence of functional GnT-I. Accordingly, the CHO cell or cell line may be further transfected or co-transfected with a nucleic acid encoding a functional or full length or wild type GnT I sequence as described in that document, should sialylation be desired.

SEQ ID NO: 1

The coding region of N-acetylglucoaminyltransferase I (Mgat1, GenBank: AF343963) mRNA isolated from the CHO JW152 cells. In these mutant cells, a C to T point mutation at position 1015 was identified (shown in bold):

ATGCTGAAGAAGCAGTCTGCAGGGCTTGTGCTTTGGGGTGCTATCCT

CTTTGTGGGCTGGAATGCCCTGCTGCTCCTCTTCTTCTGGACACGCC

CAGCCCCTGGCAGGCCCCCCTCAGATAGTGCTATCGATGATGACCCT

GCCAGCCTCACCCGTGAGGTGTTCCGCCTGGCTGAGGACGCTGAGGT

GGAGTTGGAGCGGCAGCGGGGGCTGTTGCAGCAAATCAGGGAGCATC

ATGCTTTGTGGAGACAGAGGTGGAAAGTGCCCACCGTGGCCCCTCCA

GCCTGGCCCCGTGTGCCTGCGACCCCCTCACCAGCCGTGATCCCCAT

CCTGGTCATTGCCTGTGACCGCAGCACTGTCCGGCGCTGCTTGGATA

```
AGTTGTTGCACTATCGGCCCTCAGCTGAGCATTTCCCCATCATTGTC

AGCCAGGACTGCGGGCACGAAGAGACAGCACAGGTCATTGCTTCCTA

TGGCAGTGCAGTCACACACATCCGGCAGCCAGACCTGAGTAACATCG

CTGTGCCCCCAGACCACCGCAAGTTCCAGGGTTACTACAAGATCGCC

AGGCACTACCGCTGGGCACTGGGCCAGATCTTCAACAAGTTCAAGTT

CCCAGCAGCTGTGGTAGTGGAGGACGATCTGGAGGTGGCACCAGACT

TCTTTGAGTACTTCCAGGCCACCTACCCACTGCTGAGAACAGACCCC

TCCCTTTGGTGTGTGTCTGCTTGGAATGACAATGGCAAGGAGCAGAT

GGTAGACTCAAGCAAACCTGAGCTGCTCTATCGAACAGACTTTTTC

CTGGCCTTGGCTGGCTGCTGATGGCTGAGCTGTGGACAGAGCTGGAG

CCCAAGTGGCCCAAGGCCTTCTGGGATGACTGGATGCGCAGACCTGA

GCAGCGGAAGGGGCGGGCCTGTATTCGTCCAGAAATTTCAAGAACGA

TGACCTTTGGCCGTAAGGGTGTGAGCCATGGGCAGTTCTTTGATCAG

CATCTTAAGTTCATCAAGCTGAACCAGTAGTTCGTGTCTTTCACCCA

GTTGGATTTGTCATACTTGCAGCGGGAGGCTTATGACCGGGATTTCC

TTGCCCGTGTCTATAGTGCCCCCCTGCTACAGGTGGAGAAAGTGAGG

ACCAATGATCAGAAGGAGCTGGGGGAGGTGCGGGTACAGTACACTAG

CAGAGACAGCTTCAAGGCCTTTGCTAAGGCCCTGGGTGTCATGGATG

ACCTCAAGTCTGGTGTCCCCAGAGCTGGCTACCGGGGCGTTGTCACT

TTCCAGTTCAGGGGTCGACGTGTCCACCTGGCACCCCCACAAACCTG

GGAAGGCTATGATCCTAGCTGGAATTAG
```

We further provide for mutant GnT I polypeptides, as well as fragments, variants, derivatives and homologoues thereof. The mutant GnT I polypeptide, fragment, variant, derivative or homologue may cause a CHO cell comprising it to be capable of higher expression of mannose-terminated protein, compared to a CHO cell which does not comprise such a polypeptide, for example a wild type CHO cell. The mutant GnT I polypeptide may comprise a sequence shown as SEQ ID NO: 2 or a variant, homologue, derivative or fragment thereof.

SEQ ID NO: 2

The N-acetylglucoaminyltransferase I (GnT I) protein encoded by the mutated gene in CHO JW152 cells. As a result of the point mutation (C1015T), JW152 cells only produce a truncated version of GnT I which contains only 338 amino acids rather than the normal protein that contains 447 amino acids. The C-terminal portion in bold is not translated in JW152 cells.

```
MLKKQSAGLVLWGAILFVGWNALLLLFFWTRPAPGRPPSDSAIDDDP

ASLTREVFRLAEDAEVELERQRGLLQQIREHHALWRQRWKVPTVAPP

AWPRVPATPSPAVIPILVIACDRSTVRRCLDKLLHYRPSAEHFPIIV

SQDCGHEETAQVIASYGSAVTHIRQPDLSNIAVPPDHRKFQGYYKIA

RHYRWALGQIFNKFKEPAAVVVEDDLEVAPDFFEYFQATYPLLRTDP

SLWCVSAWNDNGKEQMVDSSKPELLYRTDFFPGLGWLLMAELWTELE

PKWPKAFWDDWMRRPEQRKGRACIRPEISRTMTFGRKGVSHGQFFDQ

HLKFIKLNQQFVSFTQLDLSYLQREAYDRDFLARVYSAPLLQVEKVR

TNDQKELGEVRVQYTSRDSFKAFAKALGVMDDLKSGVPRAGYRGVVT

FQFRGRRVHLAPPQTWEGYDPSWN
```

Several of the stable lines have been adapted in suspension culture and grown in serum-free medium. Proteins of interest such as glucocerebrosidase produced in serum-free medium comprises mannose-terminated glycan structures. We therefore provide for the use of mutant CHO cells and cell lines derived from RCA-I selection, which have been adapted to suspension culture, or growth in semi-solid medium, in the production of mannose-terminated recombinant protein.

In conclusion, we have developed a novel method to express recombinant proteins with mannose-terminated glycan structures by use of glycosylation mutant host cells isolated from CHO cells by RCA-I treatment. All CHO cells that survive RCA-I treatment have very similar characteristics. First, they all lack a functional GnT I gene. Second, they express higher levels of mannose-terminated recombinant proteins than the wild type CHO cells. This feature remains the same both in transient transfection and in stably transfected cells.

The CHO glycosylation mutant cells isolated with RCA-I, such as JW152 cells, can produce recombinant glycoproteins with high degree of mannose-terminated glycan structures. This method can be used to produce recombinant glycoproteins in which presence of mannose-terminated glycan structures is important for the efficacy. These proteins include for example glucocerebrosidase, tumour-specific antigens, tumour-associated antigens and viral antigens.

MUC1

MUC1 is also known as Mucin-1, MUC-1, Breast carcinoma-associated antigen DF3, Carcinoma-associated mucin, Episialin, H23AG, PEMT, Peanut-reactive urinary mucin (PUM), Polymorphic epithelial mucin (PEM), Tumor-associated epithelial membrane antigen (EMA), Tumor-associated mucin and CD227.

MUC1 has Swiss-Prot accession number P15941.3.

Representative nucleic acid sequences of MUC1 include: Human pancreatic mucin mRNA (GenBank Accession Number: J05582.1), *Homo sapiens* mucin 1, cell surface associated (MUC1), transcript variant 1, mRNA (NCBI Reference Sequence: NM_002456.4).

Representative amino acid sequences of MUC1 include: MUC1 (*Homo sapiens*) (GenBank Accession Number: CAA56734.1), mucin-1 isoform 1 precursor (*Homo sapiens*) (NCBI Reference Sequence: NP_002447.4), mucin-1 isoform 2 precursor (*Homo sapiens*) (NCBI Reference Sequence: NP_001018016.1), mucin-1 isoform 3 precursor (*Homo sapiens*) (NCBI Reference Sequence: NP_001018017.1).

HER2/NEU

HER2 is also known as Receptor tyrosine-protein kinase erbB-2 (EC=2.7.10.1). Other names include Metastatic lymph node gene 19 protein (MLN 19), Proto-oncogene Neu, Proto-oncogene c-ErbB-2, Tyrosine kinase-type cell surface receptor HER2, p185erbB2 and CD340.

HER2 has Swiss-Prot accession number P04626.

Representative nucleic acid sequences of HER2 include: *Homo sapiens* v-erb-b2 erythroblastic leukaemia viral oncogene homologue 2, neuro/glioblastoma derived oncogene homologue (avian)(ERBB2), transcript variant 1, mRNA (NCBI Reference Sequence: NM_004448.2).

Representative amino acid sequences of HER2 include: Receptor tyrosine-protein kinase erbB-2 isoform a (*Homo sapiens*) (NCBI Reference Sequence: NP_004439.2).

Carcinoembryonic Antigen (CEA)

Carcinoembryonic antigen (CEA) may include any of the following:

carcinoembryonic antigen-related cell adhesion molecule 5 preproprotein [*Homo sapiens*] (NCBI Reference Sequence: NP_004354.2);

carcinoembryonic antigen-related cell adhesion molecule 1 isoform 1 precursor [*Homo sapiens*] (NCBI Reference Sequence: NP_001703.2);

carcinoembryonic antigen-related cell adhesion molecule 1 isoform 2 precursor [*Homo sapiens*] (NCBI Reference Sequence: NP_001020083.1)

carcinoembryonic antigen-related cell adhesion molecule 6 precursor [*Homo sapiens*] (NCBI Reference Sequence: NP_002474.3)

carcinoembryonic antigen-related cell adhesion molecule 1 isoform 3 precursor [*Homo sapiens*] (NCBI Reference Sequence: NP_001171744.1)

carcinoembryonic antigen-related cell adhesion molecule 1 isoform 4 precursor [*Homo sapiens*] (NCBI Reference Sequence: NP_001171742.1)

carcinoembryonic antigen-related cell adhesion molecule 1 isoform 5 precursor [*Homo sapiens*] (NCBI Reference Sequence: NP_001171745.1)

carcinoembryonic antigen-related cell adhesion molecule 8 precursor [*Homo sapiens*] (NCBI Reference Sequence: NP_001807.2)

pregnancy-specific beta-1-glycoprotein 5 precursor [*Homo sapiens*] (NCBI Reference Sequence: NP_002772.3)

CHO Cells and Cell Lines

The CHO cells and cell lines described here may be made by any suitable means. For example, the CHO cells and cell lines may be produced by selection using a suitable agglutinating agent, such as *Ricinus communis* agglutinin I (RCA-I).

We therefore provide a method of providing a CHO cell or cell line, the method comprising culturing CHO cells in the presence of *Ricinus communis* agglutinin I (RCA-I) and selecting cells which survive the culture.

The CHO cells and cell lines described here may be made by treating a starting or parent cell with *Ricinus communis* agglutinin I (RCA-I) and selecting cells that survive such treatment. Such surviving cells may be further cloned and made into cell lines. The selected cells and cell lines may comprise higher expression of mannose-terminated protein as described in this document. The selected cells and cell lines may comprise mutant GnT I genes and polypeptides, as described in this document.

For example, the CHO cells or cell lines described here may be selected by exposing a parent cell line to *Ricinus communis* agglutinin I (RCA-I) at a suitable concentration for a suitable period.

The RCA-1 concentration could range from between 0.1 µg/ml to 100 µg/ml, for example up to 50 µg/ml or up to 20 µg/ml. Examples of specific concentrations include 10 µg/ml and 5 µg/ml.

The period of incubation or exposure to RCA-1 could be from an hour, a few hours (such as 2, 3, 4, 5, 6, 7, 8, 9, 10, 11, 12), overnight, to a few days, such as 2 days or 3 days.

In general, the period and concentration can be adjusted to eliminate the majority of CHO cells, but to enable a small proportion of cells, which are resistant to RCA-I, to survive and form colonies. Within this, the concentration and period of exposure and selection may be varied, but generally, the higher the concentration of RCA-I, the lower the period of exposure is necessary, and vice versa.

The selection could be done on any suitable starting cell or cell line, but this will generally be a CHO cell or cell line. Any known CHO cell or cell line could be used as a starting point or parent cell, including CHO-K1. Other suitable starting cells could include, but are not limited to the following (ECACC accession numbers in brackets), CHO (85050302), CHO (PROTEIN FREE) (00102307), CHO-K1 (85051005), CHO-K1/SF (93061607), CHO/dhFr- (94060607), CHO/dhFr-AC-free (05011002), RR-CHOK1 (92052129). A starting cell or cell line may also include CHO DG44 (Catalogue number A11000-01, Invitrogen, Carlsbad, Calif., United States of America).

Following selection, the surviving cells are allowed to grow and form colonies following which they may be picked. The time allowed for this will vary, but will generally be long enough for colonies to grow to a pickable size. Examples of such times are 5 days, 7 days, 9 days, 11 days, 13 days, one week, two weeks, three weeks or more.

The picking may be done manually, or it may be automated through use of robots, such as CLONEPIX (Genetix, New Milton, Hampshire, UK). The picked colonies may be further cloned, further screened, characterised and cultured, etc.

The selected cells may be subjected to further tests. For example, they may be subjected to agglutination tests using RCA-I to confirm the mutant cells no longer react with RCA-I.

As a specific example, which is not intended to be limiting, CHO-K1 cells may be cultured, for example in 6-well plates, to confluence. Culture media may be changed to serum-free DMEM. *Ricinus communis* agglutinin I (RCA-I, EY Laboratories, San Mateo, Calif., United States of America) may be added into the media to reach a final concentration of 10 µg/gml. This may be incubated with cells overnight. The serum-free DMEM containing RCA-I may be replaced, for example with fresh DMEM with 10% FBS. Nine days later, colonies of the CHO cells that survive the RCA-I treatment may be picked and cultured, for example in 24 well plates.

These cells may be subjected to further tests, such as agglutination tests using RCA-I to confirm the mutant cells no longer react with RCA-I. We therefore provide for a method of providing a CHO cell or cell line, the method comprising culturing CHO cells in the presence of *Ricinus communis* agglutinin I (RCA-I), selecting cells which survive the culture and which do not react with RCA-I in an agglutination test.

The RCA-I selected CHO cells and CHO cell lines may be tested for their ability to produce mannose-terminated glycan structures on expressed proteins, by for example expressing a protein of interest and determining the amount of mannose-terminated glycan structures on the protein. This may be done by the methods known in the art. One example of such a method is the "Assay for Protein-Derived N-Linked Oligosaccharides", described in detail below.

We therefore provide for a method of providing a CHO cell or cell line, the method comprising culturing CHO cells in the presence of *Ricinus communis* agglutinin I (RCA-I), selecting cells which survive the culture and selecting those cells or cell lines which display higher expression of mannose-terminated proteins, and using the resulting cells or cell lines as host cells for expression of mannose-terminated recombinant proteins.

The GnT I gene in such selected cells may be cloned and sequenced, using methods known in the art. The GnT I gene may comprise a mutant GnT I gene as described here.

We therefore provide a method of providing a CHO cell or cell line, the method comprising culturing CHO cells in the presence of *Ricinus communis* agglutinin I (RCA-I), selecting cells which survive the culture and selecting those cells or cell lines which comprise mutant GnT I genes as described herein. The method may comprise a further step of expressing a recombinant protein from the CHO cell or cell line.

Assay for Protein-Derived N-Linked Oligosaccharides

The monosaccharide composition of purified expressed protein is characterized by modified high-performance anion exchange chromatography; monosaccharides are released from an aliquot of protein by heating with 4 M trifluoroacetic acid at 100 8C for 2 h and dried under a vacuum.

The monosaccharides reconstituted in sterile distilled water are analyzed using a waveform and DX500 system (DIONEX, Sunnyvale, Calif.). A CarboPac PA-1 column (DIONEX) is used to resolve monosaccharides in 18 mM sodium hydroxide solution with a flow rate of 0.8 mL/min at 35° C. as described previously (Shinkawa et al. 2003).

The oligosaccharide profile of each purified protein is characterized by modified matrix-assisted laser desorption/ionization time-of-flight mass spectrometry (MALDI-TOF MS) with a positive ion mode as described previously (Papac et al. 1998); N-linked oligosaccharides are released from 30 mg of IgG1 by incubation with 1unit of recombinant peptide-N-glycosidase F (PNGaseF; Sigma-Aldrich) for 18 h at 378C in 10 mM Tris-acetate (pH 8.3).

The released oligo-saccharides are recovered after precipitation of the protein with 75% ethanol. Following drying of the recovered supernatant, the oligosaccharides are dissolved in 13 mM acetic acid and incubated at room temperature for 2 h. The acid-treated samples are desalted with cation-exchange resin (AG50W-X8, hydrogen form; BioRad, Hercules, Calif.) and dried in a vacuum.

The dried samples are dissolved in deionized water and mixed with the matrix super-DHB solution (Bruker Daltonics) to be characterized by a MALDI-TOF MS spectrometer Reflex III (Bruker Daltonik GmbH, Bremen, Fahrenheitstr, Germany) equipped with delayed extraction.

All samples are irradiated with ultraviolet light (337 nm) from an N2 laser; positive ions are acceler-ated to 20kV and analyzed in a reflectron mode. The oligosaccharide standards (TAKARA BIO Inc., Shiga, Japan) are employed.

Mutant Cho Cells and Cell Lines

We provide for a CHO cell or cell line derived from RCA-I selection, as described above. Such a cell line could include a JW152 cell line, or any of the cell lines set out in Table E1 below, including a JW80 cell line, a JW36 cell line, a KFC15002 cell line, a KFC15071 cell line, a KFC5008 cell line, a JW152 cell line, a KFC5026 cell line, a KFC20011 cell line or a KFC15047 cell line.

Protein Expression

The CHO cells described here may be used as host cells for expression of any protein of interest. This may be done by means known in the art.

Protein expression in CHO cells and cell lines is well described in the literature, and the skilled person will have little difficulty in using the CHO cells and cell lines described here as hosts for protein expression. Thus, for example, the CHO cells and cell lines may be transfected by means known in the art with expression vectors capable of expressing the protein of interest.

The CHO cells and cell lines may further be capable of expressing wild type or functional GnT I, for example, the sequence set out in GenBank accession number AF343963. This may be done by transfecting the CHO cells and cell lines with an expression vector encoding GnT I. This may be on the same or different vector as that which contains the nucleic acid encoding the protein of interest Any suitable protein may be expressed using the CHO cells described here as host cells. The protein may comprise a heterologous protein. The protein may comprise a recombinant protein. The protein may comprise an engineered protein. The protein may comprise a glycoprotein.

Examples include heterologous proteins of therapeutic or pharmacological interest. Proteins which may be expressed include anti-EGFR mAb, α-glucosidase, laronidase, Ig-CTLA4 fusion, N-acetylgalactosamine-4-sulfatase, luteinizing hormone, anti-VEGF mAb, Factor VIII, anti-lgE mAb, anti-CD11a mAb, α-galactosidase, interferon-β, anti-TNFα mAb, erythropoietin, anti-CD52 mAb, Factor VIII, tissue plasminogen activator, anti-HER2 mAb, TNFα receptor fusion, Factor IX, follicle stimulating hormone, anti-CD20 mAb, interferon-β, β-glucocerebrosidase, deoxyribonuclease I, etc. Further examples include tumour-specific antigens, tumour-associated antigens and viral antigens, etc as described in further deail below.

In a specific example, we describe the expression of glucocerebrosidase from the CHO cells and cell lines described here.

Protein of Interest

The protein of interest which is expressed by the methods and compositions described in this document may comprise any protein. In particular, such proteins comprise those for which presence of mannose-terminated N-glycans is desired for whatever reason.

Examples of such proteins of interest include proteins for treatment of specific diseases, including glucocerebrosidase for the treatment of Gaucher disease. Other proteins of interest include proteins suitable for use as anti-cancer vaccines such as human mucin 1 (MUC1), HER2/neu and carcinoembryonic antigen (CEA), as well as antigens for use in vaccines for treatment or prophylaxis of various diseases.

As used herein, the term "antigen" refers to any substance that is capable of being the target of an immune response. An antigen may be the target of, for example, a cell-mediated and/or humoral immune response raised by a patient. The term "antigen" encompasses for example viral antigens, tumour-specific or -related antigens, bacterial antigens, parasitic antigens, allergens and the like.

Tumour Specific or Tumour Related Antigens (Anti-Cancer Vaccines)

The protein of interest may comprise a tumor-specific or tumour-related antigen, which may be suitable for use as an anti-cancer vaccine.

Tumor-specific or -related antigens include for example antigens from breast cancer, colon cancer, rectal cancer, cancer of the head and neck, renal cancer, malignant melanoma, laryngeal cancer, ovarian cancer, cervical cancer, prostate cancer. Cancer antigens are antigens which can potentially stimulate apparently tumor-specific immune responses. Some of these antigens are encoded, although not necessarily expressed, by normal cells. These antigens can be characterized as those which are normally silent (i.e., not expressed) in normal cells, those that are expressed only at certain stages of differentiation and those that are temporally expressed such as embryonic and fetal antigens. Other cancer antigens are encoded by mutant cellular genes, such as oncogenes (e.g., activated ras oncogene), suppressor genes (e.g., mutant p53), fusion proteins resulting from internal deletions or chromosomal translocations. Still other cancer antigens can be encoded by viral genes such as those carried on RNA and DNA tumor viruses. Some non-limiting examples of tumor-specific or -related antigens include MART-1/Melan-A, gp100, Dipeptidyl peptidase IV (DPPIV), adenosine deaminase-binding protein (ADAbp), cyclophilin b, Colorectal associated antigen (CRC)-C017-1A/GA733, Carcinoembryonic Antigen (CEA) and its immunogenic epitopes CAP-1 and CAP-2, etv6, aml1, Prostate Specific Antigen (PSA) and its immunogenic epitopes PSA-1, PSA-2, and PSA-3, prostate-specific membrane antigen (PSMA), T-cell receptor/CD3-zeta chain, MAGE-family of tumor antigens (e.g., MAGE-AL MAGE-A2, MAGE-A3, MAGE-A4, MAGE-A5, MAGE-A6, MAGE-A7, MAGE-A8, MAGE-A9, MAGE-A10, MAGE-A11, MAGE-A12, MAGE-Xp2 (MAGE-B2), MAGE-Xp3 (MAGE-B3), MAGE-Xp4 (MAGE-B4), MAGE-C1, MAGE-C2, MAGE-C3, MAGE-C4, MAGE-05), GAGE-family of tumor antigens (e.g., GAGE-1, GAGE-2, GAGE-3, GAGE-4, GAGE-5, GAGE-6, GAGE-7, GAGE-8, GAGE-9), BAGE, RAGE, LAGE-1, NAG, GnT-V, MUM-1, CDK4, tyrosinase, p53, MUC family (e.g. MUC-1), HER2/neu, p21ras, RCAS1, alpha-fetoprotein, E-cadherin, alpha-catenin, beta-catenin and gamma-catenin, p120ctn, gp100$^{Pmelll7}$ PRAME, NY-ESO-1, cdc27, adenomatous polyposis coli protein (APC), fodrin, Connexin 37, Ig-idiotype, p15, gp75, GM2 and GD2 gangliosides, viral products such as human papilloma virus proteins, Smad family of tumor antigens, lmp-1, P1A, EBV-encoded nuclear antigen (EBNA)-1, brain glycogen phosphorylase, SSX-1, SSX-2 (HOM-MEL-40), SSX-1, SSX-4, SSX-5, SCP-1 and CT-7, and c-erbB-2.

For example, the methods and compositions described here may be used to express cancer antigens such as human mucin 1 (MUC1), HER2/neu or carcinoembryonic antigen (CEA), or antigenic parts thereof, in recombinant forms which comprise mannose-terminated N-glycans for targeting the protein to dendritic cells and macrophages, such forms being suitable for use as or in anti-cancer vaccines.

Viral Antigens

The protein of interest may comprise a viral antigen.

Viral antigens include for example antigens from hepatitis viruses A, B, C, D & E, HIV, herpes viruses, cytomegalovirus, varicella zoster, papilloma viruses, Epstein Barr virus, influenza viruses, para-influenza viruses, adenoviruses, coxsakie viruses, picorna viruses, rotaviruses, respiratory syncytial viruses, pox viruses, rhinoviruses, rubella virus, papovirus, mumps virus, measles virus; some non-limiting examples of known viral antigens include the following: antigens derived from HIV-1 such as tat, nef, gp120 or gp160, gp40, p24, gag, env, vif, vpr, vpu, rev or part and/or combinations thereof; antigens derived from human herpes viruses such as gH, gL gM gB gC gK gE or gD or or part and/or combinations thereof or Immediate Early protein such asICP27, ICP47, ICP4, ICP36 from HSV1 or HSV2; antigens derived from cytomegalovirus, especially human cytomegalovirus such as gB or derivatives thereof; antigens derived from Epstein Barr virus such as gp350 or derivatives thereof; antigens derived from Varicella Zoster Virus such asgp1, 11, 111 and IE63; antigens derived from a hepatitis virus such as hepatitis B, hepatitis C or hepatitis E virus antigen (e.g. env protein E1 or E2, core protein, NS2, NS3, NS4a, NS4b, NSSa, NSSb, p7, or part and/or combinations thereof of HCV); antigens derived from human papilloma viruses (for example HPV6,11,16,18, e.g. L1, L2, E1, E2, E3, E4, E5, E6, E7, or part and/or combinations thereof); antigens derived from other viral pathogens, such as Respiratory Syncytial virus (e.g F and G proteins or derivatives thereof), parainfluenza virus, measles virus, mumps virus, flaviviruses (e. g. Yellow Fever Virus, Dengue Virus, Tick-borne encephalitis virus, Japanese Encephalitis Virus) or Influenza virus cells (e.g. HA, NP, NA, or M proteins, or part and/or combinations thereof).

Representative viral antigen sequences include the following:

Envelope glycoprotein B [Human herpesvirus 5 (HHV-5)] (>gi|219879660|gb IACL51135.11 envelope glycoprotein B [Human herpesvirus 5); Human herpesvirus 5 strain AD169 substrain varUC, complete genome (GenBank: FJ527563.1); Human herpesvirus 4 (Epstein-Barr virus) glycoprotein 350/220 [Human herpesvirus 4 (Epstein-Barr virus)] (GenBank: ADN85307.1), Human herpesvirus 4 isolate T41 glycoprotein 350/220 (BLLF1) gene, partial cds (GenBank: HM366438.1).

Bacterial Antigens

The protein of interest may comprise a bacterial antigen, which may be suitable for use as an anti-bacterial vaccine.

Bacterial antigens include for example antigens from Mycobacteria causing TB and leprosy, pneumocci, aerobic gram negative bacilli, mycoplasma, staphyloccocal infections, streptococcal infections, salmonellae, chlamydiae, neisseriae.

Other Antigens

The protein of interest may comprise other antigens. Other antigens include for example antigens from malaria, leishmaniasis, trypanosomiasis, toxoplasmosis, schistosomiasis, filariasis, etc.

Glucocerebrosidase Sequences

We disclose the use of glucocerebrosidase sequences at both amino acid and nucleic acid level, for the expression of glucocerebrosidase with high mannose-termination in the CHO cells anc cell lines and host cells described here.

Example glucocerebrosidase amino acid sequences include GenBank Accession Number NP_000148.2 while example glucocerebrosidase nucleic acid sequences include GenBank Accession Number NM_000157.

Mutant Gnt I Sequences

We disclose mutant GnT I sequences comprising mutant GnT I amino acid sequences and mutant GnT1 nucleic acid sequences. Example mutant GnT I amino acid sequences include the sequence shown as SEQ ID NO: 2, as well as the sequences comprising the mutations shown in column 3 of Table E1 below. Example mutant GnT I nucleic acid sequences include the sequence shown as SEQ ID NO: 1, as well as the sequences comprising the mutations shown in column 2 of Table E1 below. Table E1 shows the mutations in the GnT I sequence of clones isolated from selection with RCA-I, as described in the Examples below.

Corresponding mutations are tabulated alongside showing respective nucleotide and amino acid mutation and possible location of the disruption in secondary structure/interaction or the resulting loss in amino acids in the case of a stop codon mutation. A minimum of 4 bacteria colonies were sequenced to ensure that the mutations found were not due to PCR error.

Mutant Gnt I Polypeptides and Glucocerebrosidase Polypeptides

The CHO cells and cell lines comprise mutant GnT I polypeptides. They may be used to express proteins or polypeptides of interest, such as glucocerebrosidase polypeptides.

We therefore provide generally for a mutant GnT I polypeptide, a protein or polypeptide of interest such as a glucocerebrosidase polypeptide, together with fragments, homologues, variants and derivatives thereof. These polypeptide sequences may comprise the polypeptide sequences disclosed here, and particularly in the sequence listings.

A mutant GnT I polypeptide or protein of interest such as a glucocerebrosidase polypeptide (as the case may be) may comprise one or more changes compared to the wild type GnT I or wild type protein of interest such as a glucocerebrosidase sequence. In the case oof GnT I, mutations may result from stop codons being introduced in the encoding nucleic acid sequence and consequent premature termination of translation of the GnT I mRNA.

The mutant GnT I polypeptide may be shorter than a wild type GnT I polypeptide. It may be a truncated version of wild type GnT I polypeptide. The length of the mutant GnT I polypeptide may be 90% or less, 80% or less, 70% or less, etc than the wild type sequence.

Similarly, the polypeptide of interest may be shorter than a wild type polypeptide of interest. It may be a truncated version of wild type polypeptide of interest. The length of the polypeptide of interest may be 90% or less, 80% or less, 70% or less, etc than the wild type sequence.

For example, a polypeptide of interest or a mutant GnT I polypeptide may be missing 5, 10, 15, 20, 25, 30, 35, 40, 45, 50, 55, 60, 65, 70, 75, 80, 85, 90, 95, 100 or more C-terminal residues compared to full length or wild type GnT I or polypeptide of interest polypeptide.

The mutant GnT I polypeptide may for example comprise a sequence set out in SEQ ID NO: 2. This is the mutant GnT I polypeptide sequence from the cell line JW152. The mutant GnT I polypeptide may comprise a GnT I sequence comprising a mutation set out at column 3 of Table E1 below.

The polypeptide of interest such as a glucocerebrosidase polypeptide may for example comprise a sequence shown as GenBank Accession Number NP_000148.2.

It will be understood that the mutant GnT I and polypeptide of interest such as glucocerebrosidase polypeptide sequences disclosed here are not limited to the particular sequences set forth in the sequence listing, or fragments thereof, or sequences obtained from polypeptide of interest such as glucocerebrosidase protein or a mutant GnT I protein, but also include homologous sequences obtained from any source, for example related cellular homologues, homologues from other species and variants or derivatives thereof, provided that they have at least one of the biological activities of mutant GnT I or polypeptide of interest such as glucocerebrosidase, as the case may be.

This disclosure therefore encompasses variants, homologues or derivatives of the amino acid sequences set forth in the sequence listings, as well as variants, homologues or derivatives of the amino acid sequences encoded by the nucleotide sequences disclosed here. Where relevant to GnT I, such a sequence is generally referred to as a "mutant GnT I sequence" and where relevant to polypeptides of interest such as glucocerebrosidase, such a sequence is generally referred to as a "polypeptide sequence" or "protein sequence" or "glucocerebrosidase sequence".

The length of the polypeptide of interest such as glucocerebrosidase or mutant GnT I polypeptide may be 90% or less, 80% or less, 70% or less, etc than a corresponding wild type sequence.

For example, a mutant GnT I nucleic acid may encode a mutant GnT I polypeptide that is missing 5, 10, 15, 20, 25, 30, 35, 40, 45, 50, 55, 60, 65, 70, 75, 80, 85, 90, 95, 100 or more C-terminal residues. Similarly, a polypeptide of interest such as glucocerebrosidase nucleic acid may encode a polypeptide of interest such as glucocerebrosidase polypeptide that is missing 5, 10, 15, 20, 25, 30, 35, 40, 45, 50, 55, 60, 65, 70, 75, 80, 85, 90, 95, 100 or more C-terminal residues.

Biological Activities

In some embodiments, the sequences comprise at least one biological activity of a polypeptide of interest such as glucocerebrosidase or mutant GnT I, as the case may be. As relevant to GnT I, the biological activity may comprise improved ability to express proteins with higher mannose-terminated glycan residues compared to wild type GnT I.

As relevant to glucocerebrosidase, the biological activity may comprise ability to catalyse the hydrolysis of the glycolipid glucocerebroside to glucose and ceramide. In general, the term "glucocerebrosidase" should therefore be read as encompassing any polypeptide having glucocerebrosidase activity, including full length wild type glucocerebrosidase and variants, homologues, fragments and derivatives thereof which comprise glucocerebrosidase activity.

Any suitable assay as known in the art may be used to assay for glucocerebrosidase activity. Examples of such assays are described in Holleran, W. M., Takagi, Y., Imokawa, G., Jackson, S., Lee, J. M., Elias, P. M. 1992. β-Glucocerebrosidase activity in murine epidermis: characterization and localization in relation to differentiation. J. Lipid Res. 33:1201-1209 and Holleran, W. M., Takagi, Y., Menon, G. K., Jackson, S. M., Lee, J. M., Feingold, K. R., Elias, P. M. 1994. Permeability barrier requirements regulate epidermal β-glucocerebrosidase. J. Lipid Res. 35:905-912.

In brief, an assay for glucocerebrosidase activity may comprise use of an assay buffer consisting of citrate-phosphate buffer (pH 5.6, and 0.54% sodium taurocholate, unless otherwise indicated). The enzyme solution is preheated to 37° C. in the assay buffer (50 nl); reactions are initiated by addition of 50 μl substrate solution (0.5 mM 4-MUG in assay buffer); incubated for 60 min (37° C.); and terminated with 1.25 ml 200 mM carbonate-bicarbonate buffer, pH 10.5. Enzyme activity is determined at various pHs (pH 3.2-7.0) as the production of fluorescent 4-MU from the β-D-glucoside substrate (4-MUG). Fluorescence is measured (Ex=360 nm, Em=450 nm) with a Perkin-Elmer spectrofluorimeter. A standard 4-MU solution (0-300 nM) in carbonate-bicarbonate buffer was used for calibration.

An assay as described in detail at Example 12 below may also be employed to assay glucocerebrosidase activity.

Homologues

The polypeptides disclosed include homologous sequences obtained from any source, for example related viral/bacterial proteins, cellular homologues and synthetic peptides, as well as variants or derivatives thereof.

In the context of the present document, a homologous sequence or homologue is taken to include an amino acid sequence which is at least 60, 70, 80 or 90% identical, such as at least 95 or 98% identical at the amino acid level over at least 30, such as 50, 70, 90 or 100 amino acids with GnT I or polypeptide of interest such as glucocerebrosidase, as the case may be, for example as shown in the sequence listing herein. In the context of this document, a homologous sequence is taken to include an amino acid sequence which is at least 15, 20, 25, 30, 40, 50, 60, 70, 80 or 90% identical, such as at least 95 or 98% identical at the amino acid level, such as over at least 15, 25, 35, 50 or 100, such as 200, 300, 400 or 500 amino acids with the sequence of GnT I or polypeptide of interest such as glucocerebrosidase.

Although homology can also be considered in terms of similarity (i.e. amino acid residues having similar chemical properties/functions), in the context of the present document it is possible to express homology in terms of sequence identity. In some embodiments, the sequence identity is determined relative to the entirety of the length the relevant sequence, i.e., over the entire length or full length sequence of the relevant gene, for example.

Homology comparisons can be conducted by eye, or more usually, with the aid of readily available sequence comparison programs. These commercially available computer programs can calculate % homology between two or more sequences.

% homology may be calculated over contiguous sequences, i.e. one sequence is aligned with the other sequence and each amino acid in one sequence directly compared with the corresponding amino acid in the other sequence, one residue at a time. This is called an "ungapped" alignment. Typically, such ungapped alignments are performed only over a relatively short number of residues (for example less than 50 contiguous amino acids).

Although this is a very simple and consistent method, it fails to take into consideration that, for example, in an otherwise identical pair of sequences, one insertion or deletion will cause the following amino acid residues to be put out of alignment, thus potentially resulting in a large reduction in % homology when a global alignment is performed. Consequently, most sequence comparison methods are designed to produce optimal alignments that take into consideration possible insertions and deletions without penalising unduly the overall homology score. This is achieved by inserting "gaps" in the sequence alignment to try to maximise local homology.

However, these more complex methods assign "gap penalties" to each gap that occurs in the alignment so that, for the same number of identical amino acids, a sequence alignment with as few gaps as possible—reflecting higher relatedness between the two compared sequences—will achieve a higher score than one with many gaps. "Affine gap costs" are typically used that charge a relatively high cost for the existence of a gap and a smaller penalty for each subsequent residue in the gap. This is the most commonly used gap scoring system. High gap penalties will of course produce optimised alignments with fewer gaps. Most alignment programs allow the gap penalties to be modified. However, the default values may be used when using such software for sequence comparisons. For example when using the GCG Wisconsin Bestfit package (see below) the default gap penalty for amino acid sequences is –12 for a gap and –4 for each extension.

Calculation of maximum % homology therefore firstly requires the production of an optimal alignment, taking into consideration gap penalties. A suitable computer program for carrying out such an alignment is the GCG Wisconsin Bestfit package (University of Wisconsin, U.S.A.; Devereux et al., 1984, Nucleic Acids Research 12:387). Examples of other software than can perform sequence comparisons include, but are not limited to, the BLAST package (see Ausubel et al., 1999 ibid—Chapter 18), FASTA (Atschul et al., 1990, J. Mol. Biol., 403-410 ) and the GENEWORKS suite of comparison tools. Both BLAST and FASTA are available for offline and online searching (see Ausubel et al., 1999 ibid, pages 7-58 to 7-60).

Although the final % homology can be measured in terms of identity, the alignment process itself is typically not based on an all-or-nothing pair comparison. Instead, a scaled similarity score matrix is generally used that assigns scores to each pairwise comparison based on chemical similarity or evolutionary distance. An example of such a matrix commonly used is the BLOSUM62 matrix—the default matrix for the BLAST suite of programs. GCG Wisconsin programs generally use either the public default values or a custom symbol comparison table if supplied (see user manual for further details). The public default values for the GCG package, or in the case of other software, the default matrix, such as BLOSUM62 may be used.

Once the software has produced an optimal alignment, it is possible to calculate % homology, such as % sequence identity. The software typically does this as part of the sequence comparison and generates a numerical result.

Variants and Derivatives

The terms "variant" or "derivative" in relation to the amino acid sequences as described here includes any substitution of, variation of, modification of, replacement of, deletion of or addition of one (or more) amino acids from or to the sequence. For example, the resultant amino acid sequence retains substantially the same activity as the unmodified sequence, such as having at least the same activity as the mutant GnT I polypeptide or polypeptide of interest such as glucocerebrosidase protein shown in the sequence listings.

Polypeptides having the amino acid sequence shown in the Examples, or fragments or homologues thereof may be modified for use in the methods and compositions described here. Typically, modifications are made that maintain the biological activity of the sequence. Amino acid substitutions may be made, for example from 1, 2 or 3 to 10, 20 or 30 substitutions provided that the modified sequence retains the biological activity of the unmodified sequence. Amino acid substitutions may include the use of non-naturally occurring analogues, for example to increase blood plasma half-life of a therapeutically administered polypeptide.

Natural variants of mutant GnT I and polypeptide of interest such as glucocerebrosidase are likely to comprise conservative amino acid substitutions. Conservative substitutions may be defined, for example according to the Table below Amino acids in the same block in the second column and in the same line in the third column may be substituted for each other:

| ALIPHATIC | Non-polar | G A P |
| | | I L V |
| | Polar-uncharged | C S T M |
| | | N Q |
| | Polar-charged | D E |
| | | K R |
| AROMATIC | | H F W Y |

Fragments

Polypeptides disclosed here and useful as markers also include fragments of the above mentioned full length polypeptides and variants thereof, including fragments of the sequences set out in the sequence listings.

Polypeptides also include fragments of the full length sequence of the mutant GnT I polypeptide GnT I polypeptide, as the case may be. Such fragments may comprise at least one epitope. Methods of identifying epitopes are well known in the art. Fragments will typically comprise at least 6 amino acids, such as at least 10, 20, 30, 50 or 100 amino acids.

Included are fragments comprising, such as consisting of, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 105, 110, 115, 120, 125, 130, 135, 140, 145 or 150, or more residues from a mutant GnT I amino acid sequence or polypeptide of interest such as glucocerebrosidase amino acid sequence.

Polypeptide fragments of the mutant GnT I proteins and polypeptide of interest such as glucocerebrosidase proteins and allelic and species variants thereof may contain one or more (e.g. 5, 10, 15, or 20) substitutions, deletions or insertions, including conserved substitutions. Where substitutions, deletion and/or insertions occur, for example in different species, such as less than 50%, 40% or 20% of the amino acid residues depicted in the sequence listings are altered.

Mutant GnT I and/or polypeptide of interest such as glucocerebrosidase, and fragments, homologues, variants and derivatives, may be made by recombinant means. However, they may also be made by synthetic means using techniques well known to skilled persons such as solid phase synthesis. The proteins may also be produced as fusion proteins, for example to aid in extraction and purification. Examples of fusion protein partners include glutathione-S-transferase (GST), 6xHis, GAL4 (DNA binding and/or transcriptional activation domains) and β-galactosidase. It may also be convenient to include a proteolytic cleavage site between the fusion protein partner and the protein sequence of interest to allow removal of fusion protein sequences. The fusion protein may be such that it does not hinder the function of the protein of interest sequence. Proteins may also be obtained by purification of cell extracts from animal cells.

The polypeptide of interest such as glucocerebrosidase or mutant GnT I polypeptide, variants, homologues, fragments and derivatives disclosed here may be in a substantially isolated form. It will be understood that such polypeptides may be mixed with carriers or diluents which will not interfere with the intended purpose of the protein and still be regarded as substantially isolated. A polypeptide of interest such as glucocerebrosidase or mutant GnT I variant, homologue, fragment or derivative may also be in a substantially purified form, in which case it will generally comprise the protein in a preparation in which more than 90%, e.g. 95%, 98% or 99% of the protein in the preparation is a protein.

The polypeptide of interest such as glucocerebrosidase or mutant GnT I polypeptides variants, homologues, fragments and derivatives disclosed here may be labelled with a revealing label. The revealing label may be any suitable label which allows the polypeptide, etc to be detected. Suitable labels include radioisotopes, e.g. $^{125}$I, enzymes, antibodies, polynucleotides and linkers such as biotin. Labelled polypeptides may be used in diagnostic procedures such as immunoassays to determine the amount of a polypeptide in a sample. Polypeptides or labelled polypeptides may also be used in serological or cell-mediated immune assays for the detection of immune reactivity to said polypeptides in animals and humans using standard protocols.

Mutant GnT I or polypeptide of interest such as glucocerebrosidase polypeptide, variants, homologues, fragments and derivatives disclosed here, optionally labelled, my also be fixed to a solid phase, for example the surface of an immunoassay well or dipstick. Such labelled and/or immobilised polypeptides may be packaged into kits in a suitable container along with suitable reagents, controls, instructions and the like. Such polypeptides and kits may be used in methods of detection of antibodies to the polypeptides or their allelic or species variants by immunoassay.

Immunoassay methods are well known in the art and will generally comprise: (a) providing a polypeptide comprising an epitope bindable by an antibody against said protein; (b) incubating a biological sample with said polypeptide under conditions which allow for the formation of an antibody-antigen complex; and (c) determining whether antibody-antigen complex comprising said polypeptide is formed.

The polypeptide of interest such as glucocerebrosidase or mutant GnT I polypeptides variants, homologues, fragments and derivatives disclosed here may be used in in vitro or in vivo cell culture systems to study the role of their corresponding genes and homologues thereof in cell function, including their function in disease. For example, truncated or modified polypeptides may be introduced into a cell to disrupt the normal functions which occur in the cell. The polypeptides may be introduced into the cell by in situ expression of the polypeptide from a recombinant expression vector (see below). The expression vector optionally carries an inducible promoter to control the expression of the polypeptide.

The use of appropriate host cells, such as insect cells or mammalian cells, is expected to provide for such post-translational modifications (e.g. myristolation, glycosylation, truncation, lapidation and tyrosine, serine or threonine phosphorylation) as may be needed to confer optimal biological activity on recombinant expression products. Such cell culture systems in which the polypeptide of interest such as glucocerebrosidase or mutant GnT I polypeptide, variants, homologues, fragments and derivatives disclosed here are expressed may be used in assay systems to identify candidate substances which interfere with or enhance the functions of the polypeptides in the cell.

Mutant Gnt I Nucleic Acids

The CHO cells and cell lines comprise mutant GnT I nucleic acids.

We therefore provide generally for a mutant GnT I nucleic acid, together with fragments, homologues, variants and derivatives thereof. These nucleic acid sequences may encode the polypeptide sequences disclosed here, and particularly in the sequence listings.

The polynucleotide may comprise a mutant GnT I nucleic acid. The mutant GnT I nucleic acid may comprise one or more point mutations in the wild type GnT I sequence. Such mutations may result in corresponding changes to the amino acid sequence, or introduce stop codons and premature termination of translation of the GnT I mRNA.

The mutant GnT I nucleic acid may comprise a mutation resulting in a stop codon, which results in a mutant GnT I polypeptide being shorter than a wild type GnT I polypeptide. The length of the mutant GnT I polypeptide may be 90% or less, 80% or less, 70% or less, etc than the wild type sequence.

For example, a mutant GnT I nucleic acid may encode a mutant GnT I polypeptide that is missing 5, 10, 15, 20, 25, 30, 35, 40, 45, 50, 55, 60, 65, 70, 75, 80, 85, 90, 95, 100 or more C-terminal residues.

The mutant GnT I nucleic acid may for example comprise a sequence set out in SEQ ID NO: 1. This is the mutant GnT I nucleic acid sequence from the cell line JW152. The mutant GnT I nucleic acid may comprise a GnT I sequence comprising a mutation set out at column 2 of Table E1 below.

In particular, we provide for nucleic acids or polynucleotides which encode any of the GnT I polypeptides disclosed here. Thus, the term "GnT I sequence" should be construed accordingly. However, such a nucleic acid or polynucleotide may comprise a sequence set out as SEQ ID NO: 1, or a sequence encoding a of the corresponding polypeptide, and a fragment, homologue, variant or derivative of such a nucleic acid. The above terms therefore may be taken to refer to these sequences.

Homologues, Variants, Derivatives, and Fragments

We also provide for nucleic acids or polynucleotides which encode any of the polypeptides of interest such as glucocerebrosidase polypeptides disclosed here. Thus, the term "glucocerebrosidase sequence" should be construed accordingly. However, such a nucleic acid or polynucleotide may comprise a sequence set out as GenBank Accession Numbers NP_000148.2 or NM_000157 as the case may be, or a sequence encoding a of the corresponding polypeptide, and a fragment, homologue, variant or derivative of such a nucleic acid. The above terms therefore may be taken to refer to these sequences.

Polynucleotide

As used here in this document, the terms "polynucleotide", "nucleotide", and nucleic acid are intended to be synonymous with each other. "Polynucleotide" generally refers to any polyribonucleotide or polydeoxribonucleotide, which may be unmodified RNA or DNA or modified RNA or DNA. "Polynucleotides" include, without limitation single- and double-stranded DNA, DNA that is a mixture of single- and double-stranded regions, single- and double-stranded RNA, and RNA that is mixture of single- and double-stranded regions, hybrid molecules comprising DNA and RNA that may be single-stranded or, more typically, double-stranded or a mixture of single- and double-stranded regions. In addition, "polynucleotide" refers to triple-stranded regions comprising RNA or DNA or both RNA and DNA. The term polynucleotide also includes DNAs or RNAs containing one or more modified bases and DNAs or RNAs with backbones modified for stability or for other reasons. "Modified" bases include, for example, tritylated bases and unusual bases such as inosine. A variety of modifications has been made to DNA and RNA; thus, "polynucleotide" embraces chemically, enzymatically or metabolically modified forms of polynucleotides as typically found in nature, as well as the chemical forms of DNA and RNA characteristic of viruses and cells. "Polynucleotide" also embraces relatively short polynucleotides, often referred to as oligonucleotides.

It will be understood by a skilled person that numerous different polynucleotides and nucleic acids can encode the same polypeptide as a result of the degeneracy of the genetic code. In addition, it is to be understood that skilled persons may, using routine techniques, make nucleotide substitutions that do not affect the polypeptide sequence encoded by the polynucleotides described here to reflect the codon usage of any particular host organism in which the polypeptides are to be expressed.

Variants, Derivatives and Homologues

The polypeptide of interest such as glucocerebrosidase and mutant GnT I polynucleotides described here may comprise DNA or RNA. They may be single-stranded or double-stranded. They may also be polynucleotides which include within them synthetic or modified nucleotides. A number of different types of modification to oligonucleotides are known in the art. These include methylphosphonate and phosphorothioate backbones, addition of acridine or polylysine chains at the 3' and/or 5' ends of the molecule. For the purposes of the present document, it is to be understood that the polynucleotides described herein may be modified by any method available in the art. Such modifications may be carried out in order to enhance the in vivo activity or life span of polynucleotides.

Where the polynucleotide is double-stranded, both strands of the duplex, either individually or in combination, are encompassed by the methods and compositions described here. Where the polynucleotide is single-stranded, it is to be understood that the complementary sequence of that polynucleotide is also included.

The terms "variant", "homologue" or "derivative" in relation to a nucleotide sequence include any substitution of, variation of, modification of, replacement of, deletion of or addition of one (or more) nucleotides from or to the sequence.

As indicated above, with respect to sequence identity, a "homologue" has for example at least 5% identity, at least 10% identity, at least 15% identity, at least 20% identity, at least 25% identity, at least 30% identity, at least 35% identity, at least 40% identity, at least 45% identity, at least 50% identity, at least 55% identity, at least 60% identity, at least 65% identity, at least 70% identity, at least 75% identity, at least 80% identity, at least 85% identity, at least 90% identity, or at least 95% identity to the relevant sequence shown in the sequence listings.

There may be at least 95% identity, such as at least 96% identity, such as at least 97% identity, such as at least 98% identity, such as at least 99% identity. Nucleotide homology comparisons may be conducted as described above. A sequence comparison program that may be used is the GCG Wisconsin Bestfit program described above. The default scoring matrix has a match value of 10 for each identical nucleotide and −9 for each mismatch. The default gap creation penalty is −50 and the default gap extension penalty is −3 for each nucleotide.

In some embodiments, a mutant GnT I polynucleotide has at least 90% or more sequence identity to a sequence shown as SEQ ID NO: 1. The mutant GnT I polynucleotide may have 60% or more, such as 65% or more, 70% or more, 75% or more, 80% or more, 85% or more, 90% or more, 95% or more, 97% or more or 98% or more sequence identity to a sequence shown as SEQ ID NO: 1.

In other embodiments, a glucocerebrosidase polynucleotide has at least 90% or more sequence identity to a sequence having GenBank Accession Number NM_000157. The mutant GnT I polynucleotide may have 60% or more, such as 65% or more, 70% or more, 75% or more, 80% or more, 85% or more, 90% or more, 95% or more, 97% or more or 98% or more sequence identity to a sequence having GenBank Accession Number NM_000157.

Hybridisation

We further describe polypeptide of interest such as glucocerebrosidase and mutant GnT I nucleotide sequences that are capable of hybridising selectively to any of the sequences presented herein, or any variant, fragment or derivative thereof, or to the complement of any of the above. Nucleotide sequences are such as at least 15 nucleotides in length, such as at least 20, 30, 40 or 50 nucleotides in length.

The term "hybridisation" as used herein shall include "the process by which a strand of nucleic acid joins with a complementary strand through base pairing" as well as the process of amplification as carried out in polymerase chain reaction technologies.

Polynucleotides capable of selectively hybridising to the nucleotide sequences presented herein, or to their complement, will be generally at least 70%, such as at least 80 or 90% or such as at least 95% or 98% homologous to the corresponding nucleotide sequences presented herein over a region of at least 20, such as at least 25 or 30, for instance at least 40, 60 or 100 or more contiguous nucleotides.

The term "selectively hybridisable" means that the polynucleotide used as a probe is used under conditions where a target polynucleotide is found to hybridize to the probe at a level significantly above background. The background hybridization may occur because of other polynucleotides present, for example, in the cDNA or genomic DNA library being screened. In this event, background implies a level of signal generated by interaction between the probe and a non-specific DNA member of the library which is less than 10 fold, such as less than 100 fold as intense as the specific interaction observed with the target DNA. The intensity of interaction may be measured, for example, by radiolabelling the probe, e.g. with $^{32}P$.

Hybridisation conditions are based on the melting temperature (Tm) of the nucleic acid binding complex, as taught in Berger and Kimmel (1987, Guide to Molecular Cloning Techniques, Methods in Enzymology, Vol 152, Academic Press, San Diego Calif.), and confer a defined "stringency" as explained below.

Maximum stringency typically occurs at about Tm-5° C. (5° C. below the Tm of the probe); high stringency at about 5° C. to 10° C. below Tm; intermediate stringency at about 10°

C. to 20° C. below Tm; and low stringency at about 20° C. to 25° C. below Tm. As will be understood by those of skill in the art, a maximum stringency hybridisation can be used to identify or detect identical polynucleotide sequences while an intermediate (or low) stringency hybridisation can be used to identify or detect similar or related polynucleotide sequences.

In a one aspect, we disclose nucleotide sequences that can hybridise to a polypeptide of interest such as glucocerebrosidase and or mutant GnT I nucleic acid, or a fragment, homologue, variant or derivative thereof, under stringent conditions (e.g. 65° C. and 0.1×SSC {1×SSC=0.15 M NaCl, 0.015 M Na$_3$ Citrate pH 7.0}).

Where a polynucleotide is double-stranded, both strands of the duplex, either individually or in combination, are encompassed by the present disclosure. Where the polynucleotide is single-stranded, it is to be understood that the complementary sequence of that polynucleotide is also disclosed and encompassed.

Polynucleotides which are not 100% homologous to the sequences disclosed here but fall within the disclosure can be obtained in a number of ways. Other variants of the sequences described herein may be obtained for example by probing DNA libraries made from a range of individuals, for example individuals from different populations. In addition, other viral/bacterial, or cellular homologues particularly cellular homologues found in mammalian cells (e.g. rat, mouse, bovine and primate cells), may be obtained and such homologues and fragments thereof in general will be capable of selectively hybridising to the sequences shown in the sequence listing herein. Such sequences may be obtained by probing cDNA libraries made from or genomic DNA libraries from other animal species, and probing such libraries with probes comprising all or part of SEQ ID NO: 1 under conditions of medium to high stringency. Similar considerations apply to obtaining species homologues and allelic variants of polypeptide of interest such as glucocerebrosidase and mutant GnT I.

The polynucleotides described here may be used to produce a primer, e.g. a PCR primer, a primer for an alternative amplification reaction, a probe e.g. labelled with a revealing label by conventional means using radioactive or non-radioactive labels, or the polynucleotides may be cloned into vectors. Such primers, probes and other fragments will be at least 15, such as at least 20, for example at least 25, 30 or 40 nucleotides in length, and are also encompassed by the term polynucleotides as used herein. Fragments may be less than 500, 200, 100, 50 or 20 nucleotides in length.

Polynucleotides such as a DNA polynucleotides and probes may be produced recombinantly, synthetically, or by any means available to those of skill in the art. They may also be cloned by standard techniques.

In general, primers will be produced by synthetic means, involving a step wise manufacture of the desired nucleic acid sequence one nucleotide at a time. Techniques for accomplishing this using automated techniques are readily available in the art.

Longer polynucleotides will generally be produced using recombinant means, for example using PCR (polymerase chain reaction) cloning techniques. This will involve making a pair of primers (e.g. of about 15 to 30 nucleotides) flanking a region of the sequence which it is desired to clone, bringing the primers into contact with mRNA or cDNA obtained from an animal or human cell, performing a polymerase chain reaction under conditions which bring about amplification of the desired region, isolating the amplified fragment (e.g. by purifying the reaction mixture on an agarose gel) and recovering the amplified DNA. The primers may be designed to contain suitable restriction enzyme recognition sites so that the amplified DNA can be cloned into a suitable cloning vector.

Gaucher's Disease

[The text in this section is adapted from Gaucher's disease. (2010, March 23). In Wikipedia, The Free Encyclopedia. Retrieved 13:15, Mar. 25, 2010, from en.wikipedia.org/w/index.php?title=Gaucher %27s_disease&oldid=351623575]

Gaucher's disease is a genetic disease in which a fatty substance (lipid) accumulates in cells and certain organs. Gaucher's disease is the most common of the lysosomal storage diseases.[1]:536 It is caused by a hereditary deficiency of the enzyme glucocerebrosidase (also known as acid β-glucosidase). The enzyme acts on a fatty substance glucocerebroside (also known as glucosylceramide). When the enzyme is defective, the substance accumulates, particularly in cells of the mononuclear cell lineage. Fatty material can collect in the spleen, liver, kidneys, lungs, brain and bone marrow.

Symptoms may include enlarged spleen and liver, liver malfunction, skeletal disorders and bone lesions that may be painful, severe neurologic complications, swelling of lymph nodes and (occasionally) adjacent joints, distended abdomen, a brownish tint to the skin, anemia, low blood platelets and yellow fatty deposits on the white of the eye (sclera). Persons affected most seriously may also be more susceptible to infection. Some forms of Gaucher's disease may be treated with enzyme replacement therapy.

The disease is caused by a recessive mutation in a gene located on chromosome 1 and affects both males and females. About 1 in 100 people in the United States are carriers of the most common type of Gaucher disease, while the carrier rate among Ashkenazi Jews is 1 in 154.[2]

The disease is named after the French doctor Philippe Gaucher, who originally described it in 1882.

Classification

Gaucher's disease has three common clinical subtypes.

Type I (or non-neuropathic type) is the most common form of the disease, occurring in approximately 1 in 50,000 live births. It occurs most often among persons of Ashkenazi Jewish heritage. Symptoms may begin early in life or in adulthood and include enlarged liver and grossly enlarged spleen (together hepatosplenomegaly); the spleen can rupture and cause additional complications. Skeletal weakness and bone disease may be extensive. Spleen enlargement and bone marrow replacement cause anemia, thrombocytopenia and leukopenia. The brain is not affected, but there may be lung and, rarely, kidney impairment. Patients in this group usually bruise easily (due to low levels of platelets) and experience fatigue due to low numbers of red blood cells. Depending on disease onset and severity, type 1 patients may live well into adulthood. Many patients have a mild form of the disease or may not show any symptoms.

Type II (or acute infantile neuropathic Gaucher's disease) typically begins within 6 months of birth and has an incidence rate of approximately 1 in 100,000 live births. Symptoms include an enlarged liver and spleen, extensive and progressive brain damage, eye movement disorders, spasticity, seizures, limb rigidity, and a poor ability to suck and swallow. Affected children usually die by age 2.

Type III (the chronic neuropathic form) can begin at any time in childhood or even in adulthood, and occurs in approximately 1 in 100,000 live births. It is characterized by slowly progressive but milder neurologic symptoms compared to the acute or type 2 version. Major symptoms include an enlarged spleen and/or liver, seizures, poor coordination, skeletal irregularities, eye movement disorders, blood disorders including anemia and respiratory problems. Patients often live into their early teen years and adulthood.

These subtypes have come under some criticism for not taking account of the full spectrum of observable symptoms (the phenotypes.[1]) There are also compound heterozygous variations which considerably increase the complexity of predicting disease course.

Signs and Symptoms

Painless hepatomegaly and splenomegaly; the size of the spleen can be 1500-3000 ml, as opposed to the normal size of 50-200 ml.

Hypersplenism: the rapid and premature destruction of blood cells, leading to anemia, neutropenia and thrombocytopenia (with an increased risk of infection and bleeding)

Cirrhosis of the liver is rare

Neurological symptoms occur only in some types of Gaucher's (see below):

Type II: serious convulsions, hypertonia, mental retardation, apnea.

Type III: muscle twitches known as myoclonus, convulsions, dementia, ocular muscle apraxia.

Osteoporosis: 75% develop visible bony abnormalities due to the accumulated glucosylceramide. A deformity of the distal femur in the shape of an Erlenmeyer flask is commonly described (aseptic necrosis of the femur joint).

Yellowish-brown skin pigmentation

Pathophysiology

Acid Beta-Glucosidase

The disease is caused by a defect in the housekeeping gene lysosomal glucocerebrosidase (also known as beta-glucosidase, EC 3.2.1.45, PDB 1OGS) on the first chromosome (1q21). The enzyme is a 55.6 KD, 497 amino acids long protein that catalyses the breakdown of glucocerebroside, a cell membrane constituent of red and white blood cells. The macrophages that clear these cells are unable to eliminate the waste product, which accumulates in fibrils, and turn into Gaucher cells, which appear on light microscopy to resemble crumpled-up paper.

In the brain (type II and III), glucocerebroside accumulates due to the turnover of complex lipids during brain development and the formation of the myelin sheath of nerves.

Different mutations in the beta-glucosidase determine the remaining activity of the enzyme, and, to a large extent, the phenotype.

Heterozygotes for particular acid beta-glucosidase mutations carry about a fivefold risk of developing Parkinson's disease, making this the most common known genetic risk-factor for Parkinson's.[2][4] A study of 1525 Gaucher patients in the United States suggested that while cancer risk is not elevated, particular malignancies (non-Hodgkin lymphoma, melanoma and pancreatic cancer) occurred at a 2-3 times higher rate. [5]

Genetics

The three types of Gaucher's disease are inherited in an autosomal recessive fashion. Both parents must be carriers in order for a child to be affected. If both parents are carriers, there is a one in four, or 25%, chance with each pregnancy for an affected child. Genetic counseling and genetic testing is recommended for families who may be carriers of mutations.

Each type has been linked to particular mutations. In all, there are about 80 known mutations, grouped into three main types:[6]

Type I (N370S homozygote), the most common, also called the "non-neuropathic" type occurs mainly in Ashkenazi Jews, at 100 times the occurrence in the general populace. The median age at diagnosis is 28 years of age,[7] and life expectancy is mildly decreased[8]. There are no neurological symptoms.

Type II (1 or 2 alleles L444P) is characterized by neurological problems in small children. The enzyme is hardly released into the lysosomes. Prognosis is dismal: most die before reaching the third birthday.

Type III (also 1-2 copies of L444P, possibly delayed by protective polymorphisms) occurs in Swedish patients from the Norrbotten region. This group develops the disease somewhat later, but most die before their 30th birthday.

Diaz et al. suggest that the Gaucher-causing mutations entered the Ashkenazi Jewish gene pool in the early Middle Ages (48-55 generations ago).[9]

Diagnosis

A definitive diagnosis is made with genetic testing. As there are numerous different mutations, sequencing of the beta-glucosidase gene is sometimes necessary to confirm the diagnosis. Prenatal diagnosis is available, and is useful when there is a known genetic risk factor.

A diagnosis can also be implied by biochemical abnormalities such as high alkaline phosphatase, angiotensin-converting enzyme (ACE) and immunoglobulin levels, or by cell analysis showing "crinkled paper" cytoplasm and glycolipid-laden macrophages.

Some lysosomal enzymes are elevated, including tartrate-resistant acid phosphatase, hexosaminidase, and a human chitinase, chitotriosidase. This latter enzyme has proved to be very useful for monitoring Gaucher's disease activity in response to treatment, and may reflect the severity of the disease Treatment For type 1 and most type 3 patients, enzyme replacement treatment with intravenous recombinant glucocerebrosidase (imiglucerase) can dramatically decrease liver and spleen size, reduce skeletal abnormalities, and reverse other manifestations. This treatment costs approximately $200,000 annually for a single patient and should be continued for life or until one's finances are exhausted, whichever comes sooner. The rarity of the disease means that dose-finding studies have been difficult to conduct, so there remains controversy over the optimal dose and dosing frequency. [7] Due to the low incidence, this has become an orphan drug in many countries, meaning that a government recognizes and accommodates the financial constraints that limit research into drugs that address a small population. Velaglucerase alfa was approved by the FDA as an alternative treatment on Feb. 26, 2010. [10]

Successful bone marrow transplantation cures the non-neurological manifestations of the disease, because it introduces a monocyte population with active beta-glucosidase. However, this procedure carries significant risk and is rarely performed in Gaucher patients. Surgery to remove the spleen (splenectomy) may be required on rare occasions if the patient is anemic or when the enlarged organ affects the patient's comfort. Blood transfusion may benefit some anemic patients. Other patients may require joint replacement surgery to improve mobility and quality of life. Other treatment options include antibiotics for infections, antiepileptics for seizures, bisphosphonates for bone lesions, and liver transplants. Substrate reduction therapy may prove to be effective in stopping Type 2, as it can cross through the blood barrier into the brain. There is currently no effective treatment for the severe brain damage that may occur in patients with types 2 and 3 Gaucher disease. Gene therapy may be a future step.

Gaucher's disease has recently become a target for more than one effort at pharmacological chaperoning, which involves the use of orally administered drugs that operate at a molecular level. Miglustat is one of these oral drugs. It was approved for the treatment of this disease in 2003. As of June 2009, another oral drug, isofagomine tartrate, is under development.

Epidemiology

The National Gaucher Foundation states that around 1 in 100 people in the general U.S. population is a carrier for type 1 Gaucher's disease, giving a prevalence of 1 in 40,000: among Ashkenazi Jews the rate of carriers is considerably higher, at roughly 1 in 15.[11]

Type 2 Gaucher's disease shows no particular preference for any ethnic group. Type 3 Gaucher's disease is especially common in the population of the Northern Swedish region of Norrbotten where the incidence of the disease is 1 in 50,000.

History

The disease was first recognised by the French doctor Philippe Gaucher, who originally described it in 1882 and lent his name to the condition.[3] The biochemical basis for the disease would be elucidated in 1965.[12] The first effective treatment for the disease, the drug Ceredase, was approved by the FDA in June 1995. An improved drug, Cerezyme, was approved by the FDA in 2001 and has replaced the use of Ceredase.

Pharmaceutical Compositions

As disclosed herein, mannose-terminated recombinant proteins such as glucocerebrosidase may be used to treat or prevent disease and infection, including for example Gaucher's Disease. Other mannose-terminated recombinant proteins may be used to treat or prevent their cognate diseases, e.g., tumour-specific or tumour-associated antigens for treatment or prevention of cancer, viral antigens for treatment or prevention of viral diseases, etc Mannose-terminated recombinant proteins of interest such as glucocerebrosidase can be administered in a variety of ways including enteral, parenteral and topical routes of administration. For example, suitable modes of administration include oral, subcutaneous, transdermal, transmucosal, iontophoretic, intravenous, intramuscular, intraperitoneal, intranasal, subdural, rectal, and the like.

In accordance with other embodiments, there is provided a composition comprising a mannose-terminated recombinant proteins of interest such as glucocerebrosidase, together with a pharmaceutically acceptable carrier or excipient for the treatment or prevention of disease such as Gaucher's Disease, cancer, viral disease, etc.

Suitable pharmaceutically acceptable excipients include processing agents and drug delivery modifiers and enhancers, such as, for example, calcium phosphate, magnesium stearate, talc, monosaccharides, disaccharides, starch, gelatin, cellulose, methyl cellulose, sodium carboxymethyl cellulose, dextrose, hydroxypropyl-p-cyclodextrin, polyvinylpyrrolidinone, low melting waxes, ion exchange resins, and the like, as well as combinations of any two or more thereof. Other suitable pharmaceutically acceptable excipients are described in "Remington's Pharmaceutical Sciences," Mack Pub. Co., New Jersey (1991), incorporated herein by reference.

Pharmaceutical compositions containing mannose-terminated recombinant proteins of interest such as glucocerebrosidase may be in any form suitable for the intended method of administration, including, for example, a solution, a suspension, or an emulsion. Liquid carriers are typically used in preparing solutions, suspensions, and emulsions. Liquid carriers contemplated for use in the practice include, for example, water, saline, pharmaceutically acceptable organic solvent (s), pharmaceutically acceptable oils or fats, and the like, as well as mixtures of two or more thereof. The liquid carrier may contain other suitable pharmaceutically acceptable additives such as solubilizers, emulsifiers, nutrients, buffers, preservatives, suspending agents, thickening agents, viscosity regulators, stabilizers, and the like. Suitable organic solvents include, for example, monohydric alcohols, such as ethanol, and polyhydric alcohols, such as glycols.

Suitable oils include, for example, soybean oil, coconut oil, olive oil, safflower oil, cottonseed oil, and the like. For parenteral administration, the carrier can also be an oily ester such as ethyl oleate, isopropyl myristate, and the like. Compositions may also be in the form of microparticles, microcapsules, liposomal encapsulates, and the like, as well as combinations of any two or more thereof.

The mannose-terminated recombinant protein of interest such as glucocerebrosidase may be administered orally, parenterally, sublingually, by inhalation spray, rectally, or topically in dosage unit formulations containing conventional nontoxic pharmaceutically acceptable carriers, adjuvants, and vehicles as desired. Topical administration may also involve the use of transdermal administration such as transdermal patches or ionophoresis devices. The term parenteral as used herein includes subcutaneous injections, intravenous, intramuscular, intrastemal injection, or infusion techniques.

Injectable preparations, for example, sterile injectable aqueous or oleaginous suspensions may be formulated according to the known art using suitable dispersing or wetting agents and suspending agents. The sterile injectable preparation may also be a sterile injectable solution or suspension in a nontoxic parenterally acceptable diluent or solvent, for example, as a solution in 1,3-propanediol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

Suppositories for rectal administration of the drug can be prepared by mixing the drug with a suitable nonirritating excipient such as cocoa butter and polyethylene glycols that are solid at ordinary temperatures but liquid at the rectal temperature and will therefore melt in the rectum and release the drug.

Solid dosage forms for oral administration may include capsules, tablets, pills, powders, and granules. In such solid dosage forms, the active compound may be admixed with at least one inert diluent such as sucrose lactose or starch. Such dosage forms may also comprise, as is normal practice, additional substances other than inert diluents, e. g., lubricating agents such as magnesium stearate. In the case of capsules, tablets, and pills, the dosage forms may also comprise buffering agents. Tablets and pills can additionally be prepared with enteric coatings.

Liquid dosage forms for oral administration may include pharmaceutically acceptable emulsions, solutions, suspensions, syrups, and elixirs containing inert diluents commonly used in the art, such as water. Such compositions may also comprise adjuvants, such as wetting agents, emulsifying and suspending agents, cyclodextrins, and sweetening, flavoring, and perfuming agents.

In accordance with yet other embodiments, we provide methods for inhibiting any activity of envelope glycoprotein (E) domain III, in a human or animal subject, the method comprising administering to a subject an amount of a mannose-terminated recombinant proteins of interest such as glucocerebrosidase (or composition comprising such compound) effective to inhibit the relevant activity in the subject. Other embodiments provide methods for treating disease such as Gaucher's Disease, in a human or animal subject, comprising administering to the cell or to the human or animal subject an amount of a compound or composition as described here effective to inhibit a envelope glycoprotein (E) domain III activity in the cell or subject. The subject may be a human or non-human animal subject. Inhibition of protein activity includes detectable suppression of the relevant protein activity either as compared to a control or as compared to expected protein activity.

Effective amounts of the mannose-terminated recombinant protein of interest such as glucocerebrosidase generally include any amount sufficient to detectably inhibit the relevant protein activity by any of the assays described herein, by other assays known to those having ordinary skill in the art or by detecting an alleviation of symptoms in a subject afflicted with a disease such as Gaucher's Disease.

Successful treatment of a subject in accordance may result in the inducement of a reduction or alleviation of symptoms in a subject afflicted with a medical or biological disorder to, for example, halt the further progression of the disorder, or the prevention of the disorder. Thus, for example, treatment of disease such as Gaucher's Disease can result in a reduction in symptoms such as hepatomegaly, splenomegaly, hypersplenism, anemia, neutropenia, thrombocytopenia, risk of infection and bleeding, cirrhosis of the liver is rare, neurological symptoms, Type II symptoms such as serious convulsions, hypertonia, mental retardation, apnea, Type III symptoms such as muscle twitches known as myoclonus, convulsions, dementia, ocular muscle apraxia, osteoporosis, deformity of the distal femur, aseptic necrosis of the femur joint and yellowish-brown skin pigmentation.

The amount of active ingredient that may be combined with the carrier materials to produce a single dosage form will vary depending upon the host treated and the particular mode of administration. It will be understood, however, that the specific dose level for any particular patient will depend upon a variety of factors including the activity of the specific compound employed, the age, body weight, general health, sex, diet, time of administration, route of administration, rate of excretion, drug combination, and the severity of the particular disease undergoing therapy. The therapeutically effective amount for a given situation can be readily determined by routine experimentation and is within the skill and judgment of the ordinary clinician.

A therapeutically effective dose will generally be from about 10 µg/kg/day to 100 mg/kg/day, for example from about 25 µg/kg/day to about 20 mg/kg/day or from about 50 µg/kg/day to about 2 mg/kg/day of a mannose-terminated recombinant protein of interest such as glucocerebrosidase, which may be administered in one or multiple doses.

The mannose-terminated recombinant protein of interest such as glucocerebrosidase can also be administered in the form of liposomes. As is known in the art, liposomes are generally derived from phospholipids or other lipid substances. Liposomes are formed by mono- or multilamellar hydrated liquid crystals that are dispersed in an aqueous medium. Any non-toxic, physiologically acceptable and metabolizable lipid capable of forming liposomes can be used. The present compositions in liposome form can contain, in addition to a compound, stabilizers, preservatives, excipients, and the like. Lipids which may be used include the phospholipids and phosphatidyl cholines (lecithins), both natural and synthetic. Methods to form liposomes are known in the art. See, for example, Prescott, Ed., Methods in Cell Biology, Volume XIV, Academic Press, New York, N. W., p. 33 et seq (1976).

While the mannose-terminated recombinant protein of interest such as glucocerebrosidase can be administered as the sole active pharmaceutical agent, they can also be used in combination with one or more other agents used in the treatment of disorders. Representative agents useful in combination with the mannose-terminated recombinant protein of interest such as glucocerebrosidase for the treatment of disease such as Gaucher's Disease include, for example, recombinant glucocerebrosidase (imiglucerase), Cerazyme and Ceredase as well as any of the other treatments listed above in "Gaucher's Disease". Furthermore, any of the procedures such as surgical procedures listed there under "Treatment" may also be used in combination with administration of mannose-terminated recombinant protein such as glucocerebrosidase.

When additional active agents are used in combination with the mannose-terminated recombinant protein of interest such as glucocerebrosidase, the additional active agents may generally be employed in therapeutic amounts as indicated in the PHYSICIANS' DESK REFERENCE (PDR) 53rd Edition (1999), which is incorporated herein by reference, or such therapeutically useful amounts as would be known to one of ordinary skill in the art.

The mannose-terminated recombinant protein of interest such as glucocerebrosidase and the other therapeutically active agents can be administered at the recommended maximum clinical dosage or at lower doses. Dosage levels of the active mannose-terminated recombinant protein of interest such as glucocerebrosidase in the compositions may be varied so as to obtain a desired therapeutic response depending on the route of administration, severity of the disease and the response of the patient. The combination can be administered as separate compositions or as a single dosage form containing both agents. When administered as a combination, the therapeutic agents can be formulated as separate compositions that are given at the same time or different times, or the therapeutic agents can be given as a single composition.

Bioavailability

The compounds disclosed here (and combinations) are in some embodiments orally bioavailable. Oral bioavailablity refers to the proportion of an orally administered drug that reaches the systemic circulation. The factors that determine oral bioavailability of a drug are dissolution, membrane permeability and metabolic stability. Typically, a screening cascade of firstly in vitro and then in vivo techniques is used to determine oral bioavailablity.

Dissolution, the solubilisation of the drug by the aqueous contents of the gastro-intestinal tract (GIT), can be predicted from in vitro solubility experiments conducted at appropriate pH to mimic the GIT. The mannose-terminated recombinant protein of interest such as glucocerebrosidase may in some embodiments have a minimum solubility of 50 mg/ml. Solubility can be determined by standard procedures known in the art such as described in Adv. Drug Deliv. Rev. 23, 3-25, 1997.

Membrane permeability refers to the passage of the compound through the cells of the GIT. Lipophilicity is a key property in predicting this and is defined by in vitro Log $D_{7.4}$ measurements using organic solvents and buffer. The mannose-terminated recombinant protein of interest such as glucocerebrosidase may have a Log $D_{7.4}$ of −2 to +4 or −1 to +2. The log D can be determined by standard procedures known in the art such as described in J. Pharm. Pharmacol. 1990, 42:144.

Cell monolayer assays such as $CaCO_2$ add substantially to prediction of favourable membrane permeability in the presence of efflux transporters such as p-glycoprotein, so-called caco-2 flux. The mannose-terminated recombinant protein of interest such as glucocerebrosidase may have a caco-2 flux of greater than $2 \times 10^{-6} cms^{-1}$, for example greater than $5 \times 10^{-6} cms^{-1}$. The caco flux value can be determined by standard procedures known in the art such as described in J. Pharm. Sci, 1990, 79, 595-600.

Metabolic stability addresses the ability of the GIT or the liver to metabolise compounds during the absorption process: the first pass effect. Assay systems such as microsomes, hepatocytes etc are predictive of metabolic liability. The compounds of the Examples may in some embodiments show metabolic stability in the assay system that is commensurate with an hepatic extraction of less than 0.5. Examples of assay systems and data manipulation are described in Curr. Opin. Drug Disc. Devel., 201, 4, 36-44, Drug Met. Disp., 2000, 28, 1518-1523.

Because of the interplay of the above processes further support that a drug will be orally bioavailable in humans can be gained by in vivo experiments in animals. Absolute bioavailability is determined in these studies by administering the compound separately or in mixtures by the oral route. For absolute determinations (% absorbed) the intravenous route is also employed. Examples of the assessment of oral bioavailability in animals can be found in Drug Met. Disp., 2001, 29, 82-87; J. Med Chem, 1997, 40, 827-829, Drug Met. Disp., 1999, 27, 221-226.

The term "pharmaceutically acceptable carrier" as used herein generally refers to organic or inorganic materials, which cannot react with active ingredients. The carriers include but are not limited to sugars, such as lactose, glucose and sucrose; starches such as corn starch and potato starch; cellulose and its derivatives such as sodium carboxymethycellulose, ethylcellulose and cellulose acetates; powdered tragancanth; malt; gelatin; talc; stearic acids; magnesium stearate; calcium sulfate; vegetable oils, such as peanut oil, cotton seed oil, sesame oil, olive oil, corn oil and oil of theobroma; polyols such as propylene glycol, glycerine, sorbitol, mannitol, and polyethylene glycol; agar; alginic acids; pyrogen-free water; isotonic saline; and phosphate buffer solution; skim milk powder; as well as other non-toxic compatible substances used in pharmaceutical formulations. Wetting agents and lubricants such as sodium lauryl sulfate, as well as coloring agents, flavoring agents, lubricants, excipients, tabletting agents, stabilizers, anti-oxidants and preservatives, can also be present.

The term "therapeutically effective amount" as used herein generally refers to an amount of an agent, for example the amount of a compound as an active ingredient, that is sufficient to effect treatment as defined herein when administered to a subject in need of such treatment. A therapeutically effective amount of a compound, salt, derivative, isomer or enantiomer of the present invention will depend upon a number of factors including, for example, the age and weight of the subject, the precise condition requiring treatment and its severity, the nature of the formulation, and the route of administration, and will ultimately be at the discretion of the attendant physician or veterinarian.

However, an effective amount mannose-terminated recombinant protein for the treatment of disorders such as Gaucher's Disease, may generally be in the range of about 10 to about 40 mg/kg body weight of recipient (mammal) per day and more usually about 40 mg/kg body weight per day. Thus, for a 70 kg adult subject, the actual amount per day would typically be about 2,800 mg, and this amount may be given in a single dose per day or more usually in a number (such as two, three, four, five or six) of sub-doses per day such that the total daily dose is the same. An effective amount of a salt of the present invention may be determined as a proportion of the effective amount of the compound per se.

The term "treatment" as used herein refers to any treatment of a condition or disease in an animal, particularly a mammal, more particularly a human, and includes: preventing the disease or condition from occurring in a subject which may be predisposed to the disease but has not yet been diagnosed as having it; inhibiting the disease or condition, i.e. arresting its development; relieving the disease or condition, i.e. causing regression of the condition; or relieving the conditions caused by the disease, i.e. symptoms of the disease.

Chemical Derivative

The term "derivative" or "derivatised" as used herein includes chemical modification of a compound. Illustrative of such chemical modifications would be replacement of hydrogen by a halo group, an alkyl group, an acyl group or an amino group.

Chemical Modification

In one embodiment, the compound may be a chemically modified compound.

The chemical modification of a compound may either enhance or reduce hydrogen bonding interaction, charge interaction, hydrophobic interaction, Van Der Waals interaction or dipole interaction between the compound and the target.

In one aspect, the identified compound may act as a model (for example, a template) for the development of other compounds.

Individual

The compounds are delivered to individuals. As used herein, the term "individual" refers to vertebrates, particularly members of the mammalian species. The term includes but is not limited to domestic animals, sports animals, primates and humans.

Further Aspects

Further aspects and embodiments of the invention are now set out in the following numbered Paragraphs; it is to be understood that the invention encompasses these aspects:

Paragraph 1. A method of expressing a recombinant protein comprising mannose-terminated N-glycans from a host cell, the method comprising: (a) providing a host cell comprising a Chinese Hamster Ovary (CHO) cell which is selected with Ricinus communis agglutinin I (RCA-I) or a descendent thereof; (b) introducing a nucleic acid encoding a recombinant protein into the host cell; and (c) expressing the recombinant protein from the host cell, in which the expressed recombinant protein comprises a mannose-terminated glycan structure in which the method does not include a step of introducing functional GnT-I into the host cell.

Paragraph 2. A method according to Paragraph 1, in which the method does not include a step of introducing a nucleic acid encoding functional GnT-I into the host cell.

Paragraph 3. A method according to Paragraphs 1 or 2, in which the CHO cell selected with RCA-I or descendent thereof comprises a mutation in the GnT-I gene.

EXAMPLES

Example 1

Cell Culture

Chinese hamster ovary-K1 (CHO-K1) cells are originally obtained from Dr. Donald K. MacCallum (University of Michigan Medical Scholl, Ann Arbor, Mich.).

Parental and mutant CHO cells including JW152 cells are cultured in Dulbecco's Modified Eagle Media (DMEM) supplemented with 10% fetal bovine serum (FBS) at 37° C. in a humidified incubator with 5% $CO_2$.

Lec1.3 cells (Lec 1 cells) are kindly provided by Dr. P. Stanley (Albert Einstein College of Medicine, NY) and cultured in α-MEM (Gibco) supplemented with Proline (40 mg/L) (Invitrogen/Gibco) and 10% FBS.

Example 2

Isolation of RCA-I-Resistant CHO Cells

RCA-I-resistant CHO cells, including JW152, are isolated as described below.

CHO-K1 cells are cultured in 6-well plates to confluence before culture media is changed to serum-free DMEM. *Ricinus communis* agglutinin I (RCA-I, EY Laboratories) is added into the media to reach a final concentration of 10 μg/ml and incubated with cells overnight.

Then the serum-free DMEM containing RCA-I is replaced with fresh DMEM with 10% FBS. Nine days later, colonies of the CHO cells that survived the RCA-I treatment are picked and cultured in 24 well plates.

These cells are then subjected to agglutination tests using RCA-I to confirm the mutant cells no longer react with RCA-I.

Example 3

Cell Line JW152

As described above under "Isolation of RCA-I-Resistant CHO Cells", cell line JW152 is isolated from CHO-K1 cells by selection using a cytotoxic lectin, RCA-I. JW152 has been adapted in suspension culture and grown in serum-free medium.

The cell line JW152 was deposited on 11 Dec. 2008 at the American Type Culture Collection, 10801 University Boulevard, Manassas, Va. 20110-2209, United States of America under the accession number PTA-9657 as the International Deposition Number under the Budapest Treaty on the International Recognition of the Deposit of Microorganisms for the Purposes of Patent Procedure.

Example 4

Molecular Cloning and Sequencing Analysis of GnT I cDNA in RCA-I-Resistant CHO Cells, Including JW152

For each cell line, including JW152, $1 \times 10^7$ cells are pelleted and rinsed in PBS. Total RNA is extracted from the pellet using the RNAqueous kit (Ambion). cDNA is then synthesized through reverse transcription using Moloney Murine Leukemia virus (MMLV) reverse transcriptase (Promega) according to the manufacturer's recommendations.

The GnT I amplicon from each cell lines' cDNA is obtained through polymerase chain reaction (PCR) using PFX (Invitrogen). This is then cloned into pcDNA 3.1 expression vector and sequenced. A minimum of four clones from each mutant line are sequenced.

All plasmid purifications are carried out using mini or midi-preparation kits from Promega. Constructs are sequenced using ABI Prism 3100 Genetic Analyzer (Applied Biosystems) after cycle sequencing with Big Dye 3.1 (Applied Biosystems).

Results are shown in the following Example.

Example 5

Mutations in Gnt-I Gene of Rca-I-Resistant Cho Cells, Including JW152

TABLE E1

Table of mutations found in GnT1 mutants from clones derived from RCA-I screening. Nine CHO glycosylation mutants with different mutations in the GnT1 gene. Point mutations leading to loss in function were found in four cell lines (JW80, JW36, KFC15002, KFC15071). A point insertion resulting in the generation of a stop codon was found in KFC 5008. Mutations leading to a premature stop codon were also found in another four cell lines. (KFC5026, KFC20011, KFC15047).

| Mutant CHO Cell Line | DNA Mutation | Polypeptide Mutation (position, mutation) | Comment |
|---|---|---|---|
| JW80 | G1300C | Position 434 Ala →Pro | Domain 2 β14 |
| JW36 | A638C | Position 213 Asp → Ala | Disruption of DxD Motif, similar to JW98, JW191 |
| KFC15002 | C784G | Position 262 Arg →Gly | Domain 1 β6, similar to KFC15008 (aka 15008), KFC7501 (aka 7501) and KFC12008 |
| KFC15071 | T811A | Position 271 Trp → Arg | Domain 1 β7 |
| KFC5008 | _706C | Insertion at 706 bp Frame shift from 236 aa Asp→STOP | Stop codon generated at 245 a. a. |
| KFC5026 | G246A | Position 82 Trp→STOP | 365 a.a. missing from C terminal |
| KFC20011 | G258A | Position 86 Trp→STOP | 361 a.a. missing from C terminal |
| KFC 15047 | A859T | Position 287 Lys→STOP | 160 a.a. missing, similar to KFC15026 and KFC15072 |

The mutation of GnT1 of JW152 is determined as described above and shown in the continuation of Table E1 below.

Table of mutations found in JW152 GnT1 mutant derived from RCA-I screening. The mutation in GnT1 of JW152 leads to a premature stop codon.

| Mutant CHO Cell Line | DNA Mutation | Polypeptide Mutation (position, mutation) | Comment |
|---|---|---|---|
| JW152 | C1015T | Position 339 Gln→STOP | 108 a.a. missing from C terminal |

JW152 GnT1 Mutation

Example 6

JW152 GnT1 Nucleic Acid Sequence

The coding region of N-acetylglucoaminyltransferase I (Mgat1, GenBank: AF343963) mRNA isolated from the CHO JW152 cells is shown below.

In these mutant cells, a C to T point mutation at position 1015 was identified (shown in bold) (SEQ ID NO.1):

```
ATGCTGAAGAAGCAGTCTGCAGGGCTTGTGCTTTGGGGTGCTATCCT

CTTTGTGGGCTGGAATGCCCTGCTGCTCCTCTTCTTCTGGACACGCC
```

```
CAGCCCCTGGCAGGCCCCCCTCAGATAGTGCTATCGATGATGACCCT

GCCAGCCTCACCCGTGAGGTGTTCCGCCTGGCTGAGGACGCTGAGGT

GGAGTTGGAGCGGCAGCGGGGGCTGTTGCAGCAAATCAGGGAGCATC

ATGCTTTGTGGAGACAGAGGTGGAAAGTGCCCACCGTGGCCCCTCCA

GCCTGGCCCCGTGTGCCTGCGACCCCCTCACCAGCCGTGATCCCCAT

CCTGGTCATTGCCTGTGACCGCAGCACTGTCCGGCGCTGCTTGGATA

AGTTGTTGCACTATCGGCCCTCAGCTGAGCATTTCCCCATCATTGTC

AGCCAGGACTGCGGGCACGAAGAGACAGCACAGGTCATTGCTTCCTA

TGGCAGTGCAGTCACACACATCCGGCAGCCAGACCTGAGTAACATCG

CTGTGCCCCAGACCACCGCAAGTTCCAGGGTTACTACAAGATCGCC

AGGCACTACCGCTGGGCACTGGGCCAGATCTTCAACAAGTTCAAGTT

CCCAGCAGCTGTGGTAGTGGAGGACGATCTGGAGGTGGCACCAGACT

TCTTTGAGTACTTCCAGGCCACCTACCCACTGCTGAGAACAGACCCC

TCCCTTTGGTGTGTGTCTGCTTGGAATGACAATGGCAAGGAGCAGAT

GGTAGACTCAAGCAAACCTGAGCTGCTCTATCGAACAGACTTTTTTC

CTGGCCTTGGCTGGCTGCTGATGGCTGAGCTGTGGACAGAGCTGGAG

CCCAAGTGGCCCAAGGCCTTCTGGGATGACTGGATGCGCAGACCTGA

GCAGCGGAAGGGGCGGGCCTGTATTCGTCCAGAAATTTCAAGAACGA

TGACCTTTGGCCGTAAGGGTGTGAGCCATGGGCAGTTCTTTGATCAG

CATCTTAAGTTCATCAAGCTGAACCAGTAGTTCGTGTCTTTCACCCA

GTTGGATTTGTCATACTTGCAGCGGGAGGCTTATGACCGGGATTTCC

TTGCCCGTGTCTATAGTGCCCCCCTGCTACAGGTGGAGAAAGTGAGG

ACCAATGATCAGAAGGAGCTGGGGGAGGTGCGGGTACAGTACACTAG

CAGAGACAGCTTCAAGGCCTTTGCTAAGGCCCTGGGTGTCATGGATG

ACCTCAAGTCTGGTGTCCCCAGAGCTGGCTACCGGGGCGTTGTCACT

TTCCAGTTCAGGGGTCGACGTGTCCACCTGGCACCCCCACAAACCTG

GGAAGGCTATGATCCTAGCTGGAATTAG
```

Example 7

JW152 GnT1 Amino Acid Sequence

The N-acetylglucoaminyltransferase I (GnT I) protein encoded by the mutated gene in CHO JW152 cells, with sequence shown above, has the sequence shown below.

As a result of the point mutation (C1015T), JW152 cells only produce a truncated version of GnT I which contains only 338 amino acids rather than the normal protein that contains 447 amino acids (SEQ ID NO.2). The C-terminal portion in bold is not translated in JW152 cells.

```
MLKKQSAGLVLWGAILFVGWNALLLLFFWTRPAPGRPPSDSAIDDDP

ASLTREVFRLAEDAEVELERQRGLLQQIREHHALWRQRWKVPTVAPP

AWPRVPATPSPAVIPILVIACDRSTVRRCLDKLLHYRPSAEHFPIIV

SQDCGHEETAQVIASYGSAVTHIRQPDLSNIAVPPDHRKFQGYYKIA
```

```
RHYRWALGQIFNKFKEPAAVVVEDDLEVAPDFFEYFQATYPLLRTDP

SLWCVSAWNDNGKEQMVDSSKPELLYRTDFFPGLGWLLMAELWTELE

PKWPKAFWDDWMRRPEQRKGRACIRPEISRTMTFGRKGVSHGQFFDQ

HLKFIKLNQQFVSFTQLDLSYLQREAYDRDFLARVYSAPLLQVEKVR

TNDQKELGEVRVQYTSRDSFKAFAKALGVMDDLKSGVPRAGYRGVVT

FQFRGRRVHLAPPQTWEGYDPSWN
```

Example 8

Glucocerebrosidase Sequences

The amino acid sequence for Glucocerebrosidase (GenBank Accession Number: NP_000148.2, SEQ ID NO. 3) is:

```
>gi|54607043|ref|NP_000148.2| glucocerebrosidase
precursor [Homo sapiens] acid beta-glucosidase
gene
MAGSLTGLLLLQAVSWASGARPCIPKSFGYSSVVCVCNATYCDSFDP
PTFPALGTFSRYESTRSGRRMELSMGPIQANHTGTLLLTLQPEQKF
QKVKGFGGAMTDAAALNILALSPPAQNLLLKSYFSEEGIGYNIIRVP
MASCDFSIRTYTYADTPDDFQLHNFSLPEEDTKLKIPLIHRALQLAQ
RPVSLLASPWTSPTWLKTNGAVNGKGSLKGQPGDIYHQTWARYFVKF
LDAYAEHKLQFWAVTAENEPSAGLLSGYPPQCLGFTPEHQRDFIARD
LGPTLANSTHHNVRLLMLDDQRLLLPHWAKVVLTDPEAAKYVHGIAV
HWYLDFLAPAKATLGETHRLFPNTMLFASEACVGSKFWEQSVRLGSW
DRGMQYSHSIITNLLYHVVGWTDWNLALNPEGGPNWVRNFVDSPIIV
DITKDTFYKQPMFYHLGHFSKFIPEGSQRVGLVASQKNDLDAVALMH
PDGSAVVVVLNRSSKDVPLTIKDPAVGFLETISPGYSIHTYLWRRQ
```

The DNA sequence for the coding frame of Glucocerebrosidase (GenBank Accession Number: NM_000157, SEQ ID NO.4) is:

```
NM 000157. Homo sapiens gluc . . . [gi: 54607042]
>gi|54607042: 151-1761 Homo sapiens glucosidase,
beta; acid (includes glucosylceramidase) (GBA),
transcript variant 1, mRNA

ATGGCTGGCAGCCTCACAGGATTGCTTCTACTTCAGGCAGTGTCGTG

GGCATCAGGTGCCCGCCCCTGCATCCCTAAAAGCTTCGGCTACAGCT

CGGTGGTGTGTGTCTGCAATGCCACATACTGTGACTCCTTTGACCCC

CCGACCTTTCCTGCCCTTGGTACCTTCAGCCGCTATGAGAGTACACG

CAGTGGGCGACGGATGGAGCTGAGTATGGGCCCATCCAGGCTAATC

ACACGGGCACAGGCCTGCTACTGACCCTGCAGCCAGAACAGAAGTTC

CAGAAAGTGAAGGGATTTGGAGGGGCCATGACAGATGCTGCTGCTCT

CAACATCCTTGCCCTGTCACCCCCTGCCCAAAATTTGCTACTTAAAT

CGTACTTCTCTGAAGAAGGAATCGGATATAACATCATCCGGGTACCC

ATGGCCAGCTGTGACTTCTCCATCCGCACCTACACCTATGCAGACAC

CCCTGATGATTTCCAGTTGCACAACTTCAGCCTCCCAGAGGAAGATA

CCAAGCTCAAGATACCCCTGATTCACCGAGCCCTGCAGTTGGCCCAG

CGTCCCGTTTCACTCCTTGCCAGCCCCTGGACATCACCCACTTGGCT

CAAGACCAATGGAGCGGTGAATGGGAAGGGGTCACTCAAGGGACAGC

CCGGAGACATCTACCACCAGACCTGGGCCAGATACTTTGTGAAGTTC

CTGGATGCCTATGCTGAGCACAAGTTACAGTTCTGGGCAGTGACAGC
```

-continued

```
TGAAAATGAGCCTTCTGCTGGGCTGTTGAGTGGATACCCCTTCCAGT

GCCTGGGCTTCACCCCTGAACATCAGCGAGACTTCATTGCCCGTGAC

CTAGGTCCTACCCTCGCCAACAGTACTCACCACAATGTCCGCCTACT

CATGCTGGATGACCAACGCTTGCTGCTGCCCCACTGGGCAAAGGTGG

TACTGACAGACCCAGAAGCAGCTAAATATGTTCATGGCATTGCTGTA

CATTGGTACCTGGACTTTCTGGCTCCAGCCAAAGCCACCCTAGGGGA

GACACACCGCCTGTTCCCCAACACCATGCTCTTTGCCTCAGAGGCCT

GTGTGGGCTCCAAGTTCTGGGAGCAGAGTGTGCGGCTAGGCTCCTGG

GATCGAGGGATGCAGTACAGCCACAGCATCATCACGAACCTCCTGTA

CCATGTGGTCGGCTGGACCGACTGGAACCTTGCCCTGAACCCCGAAG

GAGGACCCAATTGGGTGCGTAACTTTGTCGACAGTCCCATCATTGTA

GACATCACCAAGGACACGTTTTACAAACAGCCCATGTTCTACCACCT

TGGCCACTTCAGCAAGTTCATTCCTGAGGGCTCCCAGAGAGTGGGGC

TGGTTGCCAGTCAGAAGAACGACCTGGACGCAGTGGCACTGATGCAT

CCCGATGGCTCTGCTGTTGTGGTCGTGCTAAACCGCTCCTCTAAGGA

TGTGCCTCTTACCATCAAGGATCCTGCTGTGGGCTTCCTGGAGACAA

TCTCACCTGGCTACTCCATTCACACCTACCTGTGGCGTCGCCAGTGA
```

Example 9

Cloning and Attachment of Restriction Sites

The coding sequence is amplified using PCR with the following primers to attach EcoRI and XhoI restriction sites:

```
Forward primer:
                                       (SEQ ID NO. 5)
GCGGAATTCGCCACCATGGCTGGCAGCCTCACAGGA Reverse primer:
                                       (SEQ ID NO. 6)
CTCGAGTCACTGGCGACGCCACAG
```

Example 10

Production of Expression Construct and Transient Expression

The coding frame is cloned into a mammalian expression vector pcDNA 3.1(+) (Invitrogen, USA) using the restriction enzymes, EcoRI and XhoI.

The resulting expression construct may be used for transient expression of recombinant human glucocerebrosidase in parental and mutant CHO cell lines using the following procedure.

Unless specified, 1 µg of DNA construct that expresses glucocerebrosidase is transfected into JW-152 mutant cells with Lipofectamine (Invitrogen) according to the manufacturer's protocols.

Two days after transfection, conditioned culture media from the transfected cells are collected. The concentrations of recombinant glucocerebrosidase in each transfection sample are determined by standard ELISA.

Example 11

Cell Transfection and Selection

The expression plasmid is transfected into the JW152 cells grown in six-well plates using Lipofectamine One day after transfection, the cells are put into selection medium. Selection medium consists of DMEM with 10% fetal bovine serum and 800 µg/ml of G418 antibiotic.

After 10-15 days, when the untransfected cells under selection medium have died, the transfected cells are deemed to be the stable pool and are then trypsinised and seeded sparsely to yield distinct single colonies which are picked and grown in 96 well plates.

After making duplicates plates, the supernatant from the 96 well plates is analysed using dot blot assay and an anti-glucocerebrosidase antibody (AbD Serotec, Japan) for detection. High producers are isolated for activity assay as described below.

20 high producers that express functionally active Glucocerebrosidase are selected to be adapted into protein-free suspension culture in 125 ml culture flasks. (HyQ PF media). Once adapted, the activity of the expressed protein is ascertained again.

The top five clones are cultured in 2 L bioreactors to characterize their productivity and the activity of the expressed protein Example 12

Glucocerebrosidase Activity Assay

The activity assay for Glucocerebrosidase activity uses a fluorescence-based assay with 4-methylumberlliferyl β-D-glucopyranoside (4 MU β-D-Glu) as a substrate.

4 MU β-D-Glu is converted to 4-methylumberlliferone (4-MU) and glucose in presence of Glucocerebrosidase. Concentrations of 4 MU are used to determine activity of glucocerebrosidase present in supernatant.

Supernatant samples are spun down to remove debris cells and transferred to clean centrifuge tubes. Samples are serially diluted 7 times with deionized MilliQ water to obtain 500 uL of each 1×, 2×, 4×, 8×, 16×, 32×, 64×, 128× diluted concentrations.

50 µL of each concentration of each sample loaded into 8 wells on 96 well plate. Loaded wells are topped up to 100 µL with 500 µL 2× Assay Buffer supplemented with 1600 ug/mL (2×) 4-methylumberlliferyl β-D-glucopyranoside (4 MU β-D-Glu) and incubated at 37° C. in a static incubator.

Enzymatic reactions in 2 wells of each concentration of each sample quenched with 100 uL of Stop Buffer at 15 min, 2 h, 4 h and 6 h respectively. Wells scanned for fluorescence using Tecan SPECTRAFluor Plus with excitation wavelength 360+/−10 nm and emission wavelength 440+/−10 nm Concentrations of 4 MU present in quenched samples compared to standard curve of 4 MU.

Standard curve of 4 MU prepared by serially diluting 1 M of 4 MU in DMSO with 1× Assay Buffer to obtain concentrations of 1× (1 mM), 2×, 4×, 8×, 16×, 32×, 64×, 128×, 256×, 512×, 1024×, 2048×, 4096×, 8192×, 16 k× and 32 k×

100 µL of each concentration of 4 MU sample loaded into 2 wells and topped to 200 µL with 100 µL of Stop Buffer.

Example 13

Purification of Expressed Glucocerebrosidase

Glucocerebrosidase is purified according to modified protocol published in Proc. Natl. Acad. Sci 1977, 74, No. 8, 3560-3563.

A decyl-agarose column (length-to-diameter ratio, 5:1) is packed and equilibrated with 0.1 M sodium citrate buffer, pH 5.0/1 mM 2-mercaptoethanol/5 mM EDTA. This buffer is used in the following steps and will be referred to hereafter as citrate buffer.

The dialyzed butanol extract is clarified by centrifugation at 5000×g for 30 min, and the supernatant is applied to the column at a ratio of 50,000 units/ml of column volume. The column is then washed with one-half column volume of citrate buffer followed by elution with an 8 column-volume linear gradient of 30-80% ethylene glycol in citrate buffer.

Glucocerebrosidase is eluted on the trailing edge of a protein peak at an ethylene glycol concentration of approximately 60%. Fractions with high specific activity are pooled and diluted 1:3 with citrate buffer.

An octyl-Sepharose column (length-to-diameter ratio, 5:1) is packed, washed for 12 hr with 0.1 M NaOH, and equilibrated with citrate buffer prepared in pyrogen-free 0.9% (wt/vol) saline. The enzyme sample is applied at a ratio of 300,000 units/ml of column volume. The column is washed with one-half column volume of pyrogen-free citrate buffer.

Approximately-40% of the inactive protein did not adsorb to the column, and the enzyme is eluted at about 60% ethylene glycol concentration.

The fractions from the octyl-Sepharose column with high specific activity are pooled, diluted by one-third with 60% ethylene glycol in 0.9% saline, and made 0.5 mg/ml in human serum albumin. This enzyme solution is added rapidly to three volumes of cold 95% ethanol, stirred well, and held in the cold for 1 hr before centrifugation at 4000×g for 5 min.

The supernatant is discarded and the precipitate is suspended in 200 volumes (wt/vol) of an ethanol/glycerol solution (three volumes of 95% ethanol and one volume of 60% pyrogen-free glycerol); the suspension is centrifuged as above. The wash is repeated twice more and the final precipitate is taken up in human serum albumin solution (40 mg/ml in 0.9% saline) to a concentration of approximately 106 units/ml.

Example 14

Mass Spectrometry of N-glycans Produced by JW152

EPO-Fc was expressed in wild type CHO-K1 cells and JW152 cells and purified by affinity chromatography. N-glycans were released from purified EPO-Fc and analyzed by Mass spectrometry (MS).

Figure 7:
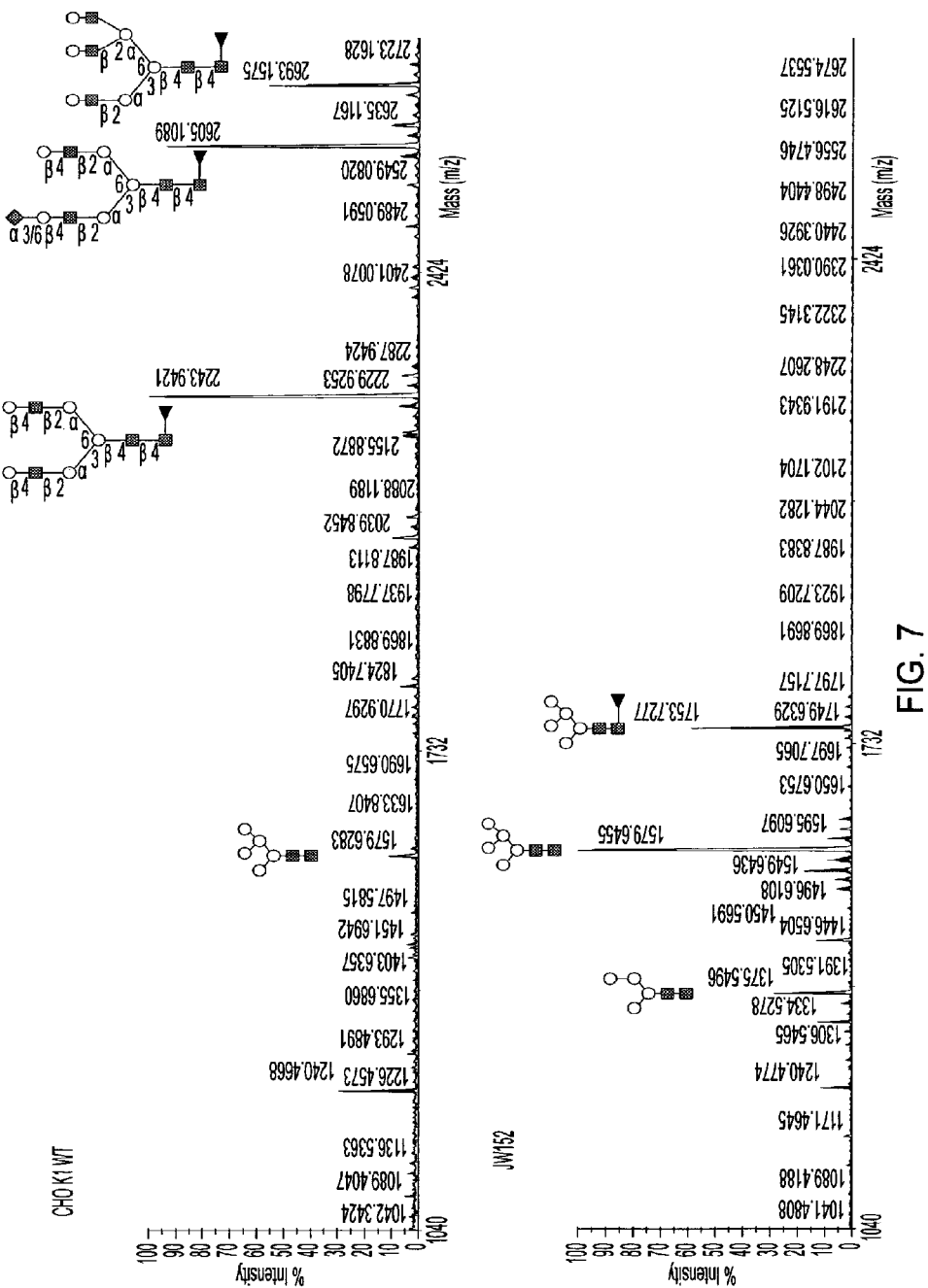
FIG. 7 is a drawing showing a comparison of N-glycosylation of EPO-FC produced in CHO WT and JW152 cells.
Figure 7:
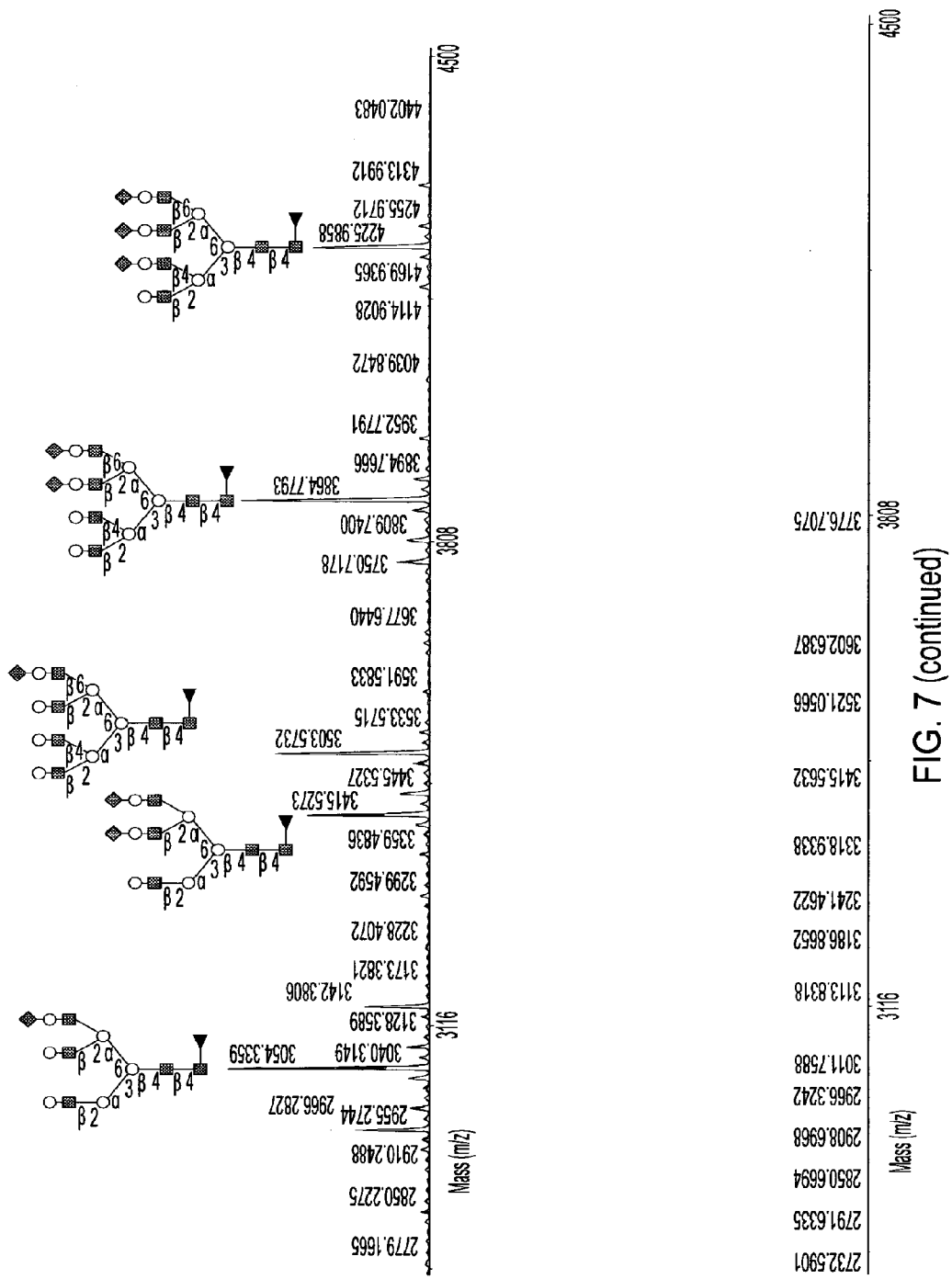
Figure 8:
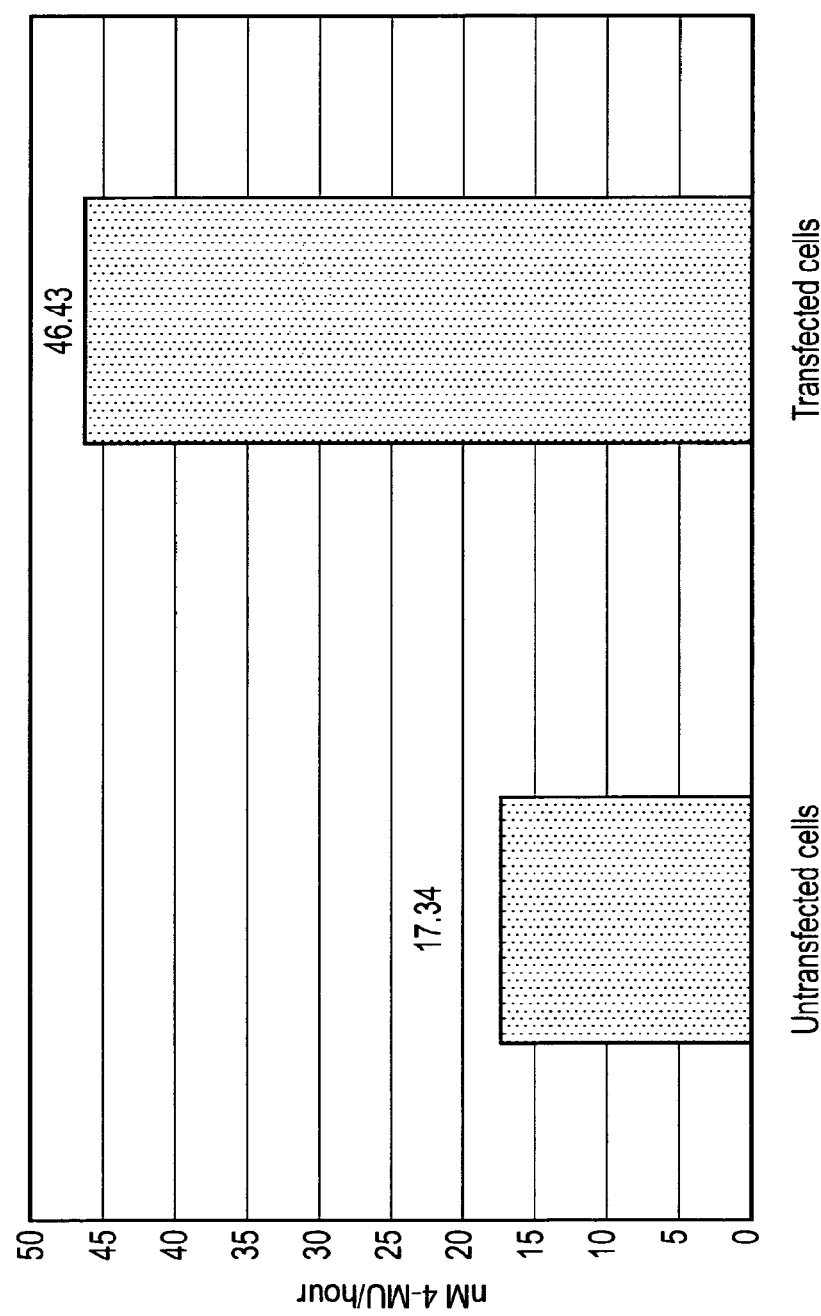
FIG. 8 is a drawing showing a comparison of glucocerebrosidase activity in supernatant of transfected cells and untransfected cells.

The results are shown in FIG. 7. Mass spectrometry results of N-glycans produced by wild-type CHO-K1 cells are shown on the top panel and those produced by JW152 cells are shown at the bottom panel.

As can be seen, CHO-K1 cells produced all kinds of N-glycans. However, JW152 cells produced only mannose-terminated N-glycans: Man5GlcNAc2, fucosylated Man5GlcNAc2 and Man4GlcNAc.

Example 15

Comparison of Glucocerebrosidase Activity in Supernatant of Transfected Cells and Untransfected Cells Culture supernatant is incubated with 4-methylumbelliferyl®-D -glucopyranoside in a citrate buffer (pH 5.9).

After one hour, the reaction is quenched with addition of 0.2M glycine adjusted to pH 10.5.

4-methylumbelliferone (4-MU) gives peak fluorescence activity above pH 10. Fluorescence is measured at λex 365 nm; λm 445 nm.

A standard curve is generated from dilution of 4-MU reagent. The activity is based on measured amount of 4-MU released in one hour. When Glucocerebrosidase was expressed in JW152 cells, the higher activity was observed in the culture medium.

References

References 1 to 10 are for the section headed "Gaucher's Disease" above.

1. James, William D.; Berger, Timothy G.; et al. (2006). Andrews' Diseases of the Skin: clinical Dermatology. Saunders Elsevier. ISBN 0-7216-2921-0.
2. a b Jacquelyn K Beals (Nov. 19, 2008), "ASHG 2008: Gaucher Disease Mutation Carriers at Higher Risk for Parkinson's Disease", Medscape Medical News
3. a b Gaucher PCE (1882). De l'epithelioma primitif de la rate, hypertrophie idiopathique de la rate sans leucemie [academic thesis]. Paris, France.
4. Aharon-Peretz J, Rosenbaum H, Gershoni-Baruch R (2004). "Mutations in the glucocerebrosidase gene and Parkinson's disease in Ashkenazi Jews". N. Engl. J. Med. 351 (19): 1972-7. doi:10.1056/NEJMoa033277. PMID 15525722.
5. Landgren O, Turesson I, Gridley G, Caporaso N E (2007). "Risk of Malignant Disease Among 1525 Adult Male US Veterans With Gaucher Disease". Archives of Internal Medicine 167 (11): 1189-1194. doi:10.1001/archinte.167.11.1189. PMID 17563029.
6. Online 'Mendelian Inheritance in Man' (OMIM) 606463
7. a b Grabowski G A (2008). "Phenotype, diagnosis, and treatment of Gaucher's disease". Lancet 372: 1263-1271. doi:10.1016/S0140-6736(08)61522-6.
8. Weinreb N J, Deegan P, Kacena K A, et al. (December 2008). "Life expectancy in Gaucher disease type 1". Am. J. Hematol. 83 (12): 896-900. doi:10.1002/ajh.21305. PMID 18980271.
9. Diaz G A, Gelb B D, Risch N, et al. (2000). "Gaucher disease: the origins of the Ashkenazi Jewish N370S and 84GG acid beta-glucosidase mutations". Am. J. Hum. Genet. 66 (6): 1821-32. doi:10.1086/302946. PMID 10777718.
10. www.medicalnewstoday.com/articles/180630.php
11. "National Gaucher Foundation". Retrieved 2007 May 30.
12. Brady R O, Kanfer J N, Shapiro D (1965). "Metabolism of glucocerebrosides. II. Evidence of an enzymatic deficiency in Gaucher's disease". Biochem. Biophys. Res. Commun. 18: 221-5. doi:10.1016/0006-291X(65)90743-6. PMID 14282020.
13. geneticpeople.com/?p=276
14. www.nlm.nih.gov/medlineplus/ency/imagepages/1450.htm
15. Dvir et al., EMBO Reports, 2003, 4:704
16. Helenius & Aebi, Science, 2001, 291:2364

Each of the applications and patents mentioned in this document, and each document cited or referenced in each of the above applications and patents, including during the prosecution of each of the applications and patents ("application cited documents") and any manufacturer's instructions or catalogues for any products cited or mentioned in each of the applications and patents and in any of the application cited documents, are hereby incorporated herein by reference. Furthermore, all documents cited in this text, and all documents cited or referenced in documents cited in this text, and any manufacturer's instructions or catalogues for any products cited or mentioned in this text, are hereby incorporated herein by reference.

Various modifications and variations of the described methods and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in molecular biology or related fields are intended to be within the scope of the claims.

The invention claimed is:

1. A recombinant protein comprising mannose-terminated N-glycans expressed by a host cell line according to a method which includes steps of:
   (a) introducing a nucleic acid encoding a recombinant protein into a host cell comprising a mutation in the GnT I gene leading to loss of GnT I function, wherein the host cell is a Chinese Hamster Ovary (CHO) cell selected with Ricinus communis agglutinin I (RCA-I) or a descendent thereof; and
   (b) expressing the recombinant protein from the host cell, wherein the expressed recombinant protein comprises mannose-terminated N-glycans and the method does not include a step of introducing functional GnT I into the host cell.

2. The recombinant protein comprising mannose-terminated N-glycans according to claim 1, wherein the recombinant protein has glucocerebrosidase activity.

3. The recombinant protein comprising mannose-terminated N-glycans according to claim 1, wherein the recombinant protein is MUC1.

4. The recombinant protein comprising mannose-terminated N-glycans according to claim 1, wherein the recombinant protein is HER2/neu.

5. The recombinant protein comprising mannose-terminated N-glycans according to claim 1, wherein the recombinant protein is carcinoembryonic antigen (CEA).

6. A method comprising expressing a recombinant protein comprising mannose-terminated N-glycans from a host cell according to claim 1, and administering the recombinant protein comprising mannose-terminated N-glycans to an individual suffering from or at risk of suffering from:
   a cancer and the recombinant protein comprising mannose-terminated N-glycans is a tumor antigen;
   Gaucher's disease and the recombinant protein comprising mannose-terminated N-glycans has glucocerebrosidase activity;
   a viral associated or caused disease and the recombinant protein comprising mannose-terminated N-glycans is a viral antigen;
   a bacterial associated or caused disease and the recombinant protein comprising mannose-terminated N-glycans is a bacterial antigen;
   a parasite associated or caused disease and the recombinant protein comprising mannose-terminated N-glycans is a parasitic antigen; or
   an allergic disease and the recombinant protein comprising mannose-terminated N-glycans is an allergen.

7. The method according to claim 6, wherein the recombinant protein comprising mannose-terminated N-glycans is MUC1, and the individual is suffering from or at risk of suffering from a cancer.

8. The method according to claim 6, wherein the recombinant protein comprising mannose-terminated N-glycans is HER2/neu, and the individual is suffering from or at risk of suffering from a cancer.

9. The method according to claim 6, wherein the recombinant protein comprising mannose-terminated N-glycans is carcinoembryonic antigen (CEA), and the individual is suffering from or at risk of suffering from a cancer.

10. The method according to claim 6, wherein the recombinant protein comprising mannose-terminated N-glycans has glucocerebrosidase activity, and the individual is suffering from Gaucher's disease.

11. A method comprising administering a recombinant protein comprising mannose-terminated N-glycans according to claim 1 to an individual suffering from or at risk of suffering from:
   a cancer and the recombinant protein comprising mannose-terminated N-glycans is a tumor antigen;
   Gaucher's disease and the recombinant protein comprising mannose-terminated N-glycans has glucocerebrosidase activity;
   a viral associated or caused disease and the recombinant protein comprising mannose-terminated N-glycans is a viral antigen;

a bacterial associated or caused disease and the recombinant protein comprising mannose-terminated N-glycans is a bacterial antigen;

a parasite associated or caused disease and the recombinant protein comprising mannose-terminated N-glycans is a parasitic antigen; or an allergic disease and the recombinant protein comprising mannose-terminated N-glycans is an allergen.

12. The method according to claim 11, wherein the recombinant protein comprising mannose-terminated N-glycans is MUC1 and the individual is suffering from or at risk of suffering from a cancer.

13. The method according to claim 11, wherein the recombinant protein comprising mannose-terminated N-glycans is HER2/neu, and the individual is suffering from or at risk of suffering from a cancer.

14. The method according to claim 11, wherein the recombinant protein comprising mannose-terminated N-glycans is carcinoembryonic antigen (CEA), and the individual is suffering from or at risk of suffering from a cancer.

15. The method according to claim 11, wherein the recombinant protein comprising mannose-terminated N-glycans has glucocerebrosidase activity, and the individual is suffering from Gaucher's disease.

16. The method according to claim 6, wherein the recombinant protein comprising mannose-terminated N-glycans is a viral antigen selected from the group consisting of antigens from hepatitis viruses A, B, C, D & E, HIV, herpes viruses, cytomegalovirus, varicella zoster, papilloma viruses, Epstein Barr virus, influenza viruses, para-influenza viruses, adenoviruses, coxsakie viruses, picorna viruses, rotaviruses, respiratory syncytial viruses, pox viruses, rhinoviruses, rubella virus, papovirus, mumps virus, and measles virus, and the individual is suffering from a viral associated or caused disease.

17. The method according to claim 16, wherein the viral antigen is selected from the group consisting of HIV-1 antigens tat, nef, gp120 or gp160, gp40, p24, gag, env, vif, vpr, vpu, rev or part and/or combinations thereof; human herpes virus antigens gH, gL, gM, gB, gC, gK, gE, gD, or part and/or combinations thereof, Immediate Early proteins ICP27, ICP47, ICP4, ICP36 from HSV1 or HSV2; cytomegalovirus antigens gB or derivatives thereof; Epstein Barr virus antigens gp350 or derivatives thereof; Varicella Zoster Virus antigens asgp1, 11, 111 and IE63; hepatitis virus antigens env protein E1, env protein E2, core protein, NS2, NS3, NS4a, NS4b, NSSa, NSSb, p7, or part and/or combinations thereof; human papilloma virus antigens L1, L2, E1, E2, E3, E4, E5, E6, E7, or part and/or combinations thereof; Respiratory Syncytial virus antigens F and G proteins or derivatives thereof; parainfluenza virus antigens; measles virus antigens; mumps virus antigens; flavivirus antigens; and Influenza virus antigens HA, NP, NA, M proteins, or part and/or combinations thereof, and the individual is suffering from a viral associated or caused disease.

18. The method according to claim 16, wherein the viral antigen is selected from the group consisting of Human herpesvirus 5 envelope glycoprotein B and Human herpesvirus 4 (Epstein-Barr virus) glycoprotein 350/220, and the individual is suffering from a viral associated or caused disease.

19. The method according to claim 6, wherein the recombinant protein comprising mannose-terminated N-glycans is a bacterial antigen selected from the group consisting of antigens from Mycobacteria causing TB and leprosy, pneumocci, aerobic gram negative bacilli, mycoplasma, bacteria causing staphyloccocal infections, bacteria causing streptococcal infections, bacteria causing salmonellae, bacteria causing chlamydiae, and bacteria causing neisseriae, and the individual is suffering from a bacterial associated or caused disease.

20. The method according to claim 6, wherein the recombinant protein comprising mannose-terminated N-glycans is a parasitic antigen selected from the group consisting of antigens from parasites causing malaria, leishmaniasis, trypanosomiasis, toxoplasmosis, schistosomiasis, and filariasis, and the individual is suffering from a parasite associated or caused disease.

21. The method according to claim 11, wherein the recombinant protein comprising mannose-terminated N-glycans is a viral antigen selected from the group consisting of antigens from hepatitis viruses A, B, C, D & E, HIV, herpes viruses, cytomegalovirus, varicella zoster, papilloma viruses, Epstein Barr virus, influenza viruses, para-influenza viruses, adenoviruses, coxsakie viruses, picorna viruses, rotaviruses, respiratory syncytial viruses, pox viruses, rhinoviruses, rubella virus, papovirus, mumps virus, and measles virus, and the individual is suffering from a viral associated or caused disease.

22. The method according to claim 21, wherein the viral antigen is selected from the group consisting of HIV-1 antigens tat, nef, gp120 or gp160, gp40, p24, gag, env, vif, vpr, vpu, rev or part and/or combinations thereof; human herpes virus antigens gH, gL, gM, gB, gC, gK, gE, gD, or part and/or combinations thereof, Immediate Early proteins ICP27, ICP47, ICP4, ICP36 from HSV1 or HSV2; cytomegalovirus antigens gB or derivatives thereof; Epstein Barr virus antigens gp350 or derivatives thereof; Varicella Zoster Virus antigens asgp1, 11, 111 and IE63; hepatitis virus antigens env protein E1, env protein E2, core protein, NS2, NS3, NS4a, NS4b, NSSa, NSSb, p7, or part and/or combinations thereof; human papilloma virus antigens L1, L2, E1, E2, E3, E4, E5, E6, E7, or part and/or combinations thereof; Respiratory Syncytial virus antigens F and G proteins or derivatives thereof; parainfluenza virus antigens; measles virus antigens; mumps virus antigens; flavivirus antigens; and Influenza virus antigens HA, NP, NA, M proteins, or part and/or combinations thereof, and the individual is suffering from a viral associated or caused disease.

23. The method according to claim 21, wherein the viral antigen is selected from the group consisting of Human herpesvirus 5 envelope glycoprotein B and Human herpesvirus 4 (Epstein-Barr virus) glycoprotein 350/220, and the individual is suffering from a viral associated or caused disease.

24. The method according to claim 11, wherein the recombinant protein comprising mannose-terminated N-glycans is a bacterial antigen selected from the group consisting of antigens from Mycobacteria causing TB and leprosy, pneumocci, aerobic gram negative bacilli, mycoplasma, bacteria causing staphyloccocal infections, bacteria causing streptococcal infections, bacteria causing salmonellae, bacteria causing chlamydiae, and bacteria causing neisseriae, and the individual is suffering from a bacterial associated or caused disease.

25. The method according to claim 11, wherein the recombinant protein comprising mannose-terminated N-glycans is a parasitic antigen selected from the group consisting of antigens from parasites causing malaria, leishmaniasis, trypanosomiasis, toxoplasmosis, schistosomiasis, and filariasis, and the individual is suffering from a parasite associated or caused disease.

\* \* \* \* \*

SEQUENCE LISTING

```
<160> NUMBER OF SEQ ID NOS: 6

<210> SEQ ID NO 1
<211> LENGTH: 1344
<212> TYPE: DNA
<213> ORGANISM: Cricetulus griseus

<400> SEQUENCE: 1
atgctgaaga agcagtctgc agggcttgtg ctttggggtg ctatcctctt tgtgggctgg      60
aatgccctgc tgctcctctt cttctggaca cgcccagccc ctggcaggcc ccctcagat     120 agtgctatcg atgatgaccc tgccagcctc acccgtgagg tgttccgcct ggctgaggac    180
gctgaggtgg agttggagcg gcagcggggg ctgttgcagc aaatcaggga gcatcatgct    240
ttgtggagac agaggtggaa agtgcccacc gtggcccctc cagcctggcc ccgtgtgcct    300 gcgacccct caccagccgt gatccccatc ctggtcattg cctgtgaccg cagcactgtc    360
cggcgctgct tggataagtt gttgcactat cggccctcag ctgagcattt ccccatcatt    420
gtcagccagg actgcgggca cgaagagaca gcacaggtca ttgcttccta tggcagtgca    480
gtcacacaca tccggcagcc agacctgagt aacatcgctg tgcccccaga ccaccgcaag    540
ttccagggtt actacaagat cgccaggcac taccgctggg cactgggcca gatcttcaac    600
aagttcaagt tcccagcagc tgtggtagtg gaggacgatc tggaggtggc accagacttc    660
tttgagtact tccaggccac ctacccactg ctgagaacag acccctccct ttggtgtgtg    720
tctgcttgga atgacaatgg caaggagcag atggtagact caagcaaacc tgagctgctc    780
tatcgaacag actttttttcc tggccttggc tggctgctga tggctgagct gtggacagag    840
ctggagccca gtggcccaa ggccttctgg gatgactgga tgcgcagacc tgagcagcgg    900 aagggcggg cctgtattcg tccagaaatt tcaagaacga tgacctttgg ccgtaagggt    960
gtgagccatg ggcagttctt tgatcagcat cttaagttca tcaagctgaa ccagtagttc   1020
gtgtctttca cccagttgga tttgtcatac ttgcagcggg aggcttatga ccgggatttc   1080
cttgcccgtg tctatagtgc cccctgcta caggtggaga aagtgaggac caatgatcag   1140
aaggagctgg gggaggtgcg ggtacagtac actagcagag acagcttcaa ggcctttgct   1200
aaggccctgg gtgtcatgga tgacctcaag tctggtgtcc ccagagctgg ctaccggggc   1260
gttgtcactt tccagttcag gggtcgacgt gtccacctgg cacccccaca aacctgggaa   1320
ggctatgatc ctagctggaa ttag                                          1344

<210> SEQ ID NO 2
<211> LENGTH: 447
<212> TYPE: PRT
<213> ORGANISM: Cricetulus griseus

<400> SEQUENCE: 2

Met Leu Lys Lys Gln Ser Ala Gly Leu Val Leu Trp Gly Ala Ile Leu
1               5                   10                  15

Phe Val Gly Trp Asn Ala Leu Leu Leu Phe Phe Trp Thr Arg Pro
                20                  25                  30
```

```
Ala Pro Gly Arg Pro Pro Ser Asp Ser Ala Ile Asp Asp Pro Ala
         35                  40                  45
Ser Leu Thr Arg Glu Val Phe Arg Leu Ala Glu Asp Ala Glu Val Glu
 50                  55                  60
Leu Glu Arg Gln Arg Gly Leu Leu Gln Gln Ile Arg Glu His His Ala
 65                  70                  75                  80
Leu Trp Arg Gln Arg Trp Lys Val Pro Thr Val Ala Pro Pro Ala Trp
                 85                  90                  95
Pro Arg Val Pro Ala Thr Pro Ser Pro Ala Val Ile Pro Ile Leu Val
                100                 105                 110
Ile Ala Cys Asp Arg Ser Thr Val Arg Arg Cys Leu Asp Lys Leu Leu
            115                 120                 125
His Tyr Arg Pro Ser Ala Glu His Phe Pro Ile Ile Val Ser Gln Asp
        130                 135                 140
Cys Gly His Glu Glu Thr Ala Gln Val Ile Ala Ser Tyr Gly Ser Ala
145                 150                 155                 160
Val Thr His Ile Arg Gln Pro Asp Leu Ser Asn Ile Ala Val Pro Pro
                165                 170                 175
Asp His Arg Lys Phe Gln Gly Tyr Tyr Lys Ile Ala Arg His Tyr Arg
                180                 185                 190
Trp Ala Leu Gly Gln Ile Phe Asn Lys Phe Lys Phe Pro Ala Ala Val
            195                 200                 205
Val Val Glu Asp Asp Leu Glu Val Ala Pro Asp Phe Phe Glu Tyr Phe
        210                 215                 220
Gln Ala Thr Tyr Pro Leu Leu Arg Thr Asp Pro Ser Leu Trp Cys Val
225                 230                 235                 240
Ser Ala Trp Asn Asp Asn Gly Lys Glu Gln Met Val Asp Ser Ser Lys
                245                 250                 255
Pro Glu Leu Leu Tyr Arg Thr Asp Phe Phe Pro Gly Leu Gly Trp Leu
                260                 265                 270
Leu Met Ala Glu Leu Trp Thr Glu Leu Glu Pro Lys Trp Pro Lys Ala
            275                 280                 285
Phe Trp Asp Asp Trp Met Arg Arg Pro Glu Gln Arg Lys Gly Arg Ala
        290                 295                 300
Cys Ile Arg Pro Glu Ile Ser Arg Thr Met Thr Phe Gly Arg Lys Gly
305                 310                 315                 320
Val Ser His Gly Gln Phe Phe Asp Gln His Leu Lys Phe Ile Lys Leu
                325                 330                 335
Asn Gln Gln Phe Val Ser Phe Thr Gln Leu Asp Leu Ser Tyr Leu Gln
            340                 345                 350
Arg Glu Ala Tyr Asp Arg Asp Phe Leu Ala Arg Val Tyr Ser Ala Pro
        355                 360                 365
Leu Leu Gln Val Glu Lys Val Arg Thr Asn Asp Gln Lys Glu Leu Gly
    370                 375                 380
Glu Val Arg Val Gln Tyr Thr Ser Arg Asp Ser Phe Lys Ala Phe Ala
385                 390                 395                 400
Lys Ala Leu Gly Val Met Asp Asp Leu Lys Ser Gly Val Pro Arg Ala
                405                 410                 415
Gly Tyr Arg Gly Val Val Thr Phe Gln Phe Arg Gly Arg Val His
                420                 425                 430
Leu Ala Pro Pro Gln Thr Trp Glu Gly Tyr Asp Pro Ser Trp Asn
            435                 440                 445
```

-continued

```
<210> SEQ ID NO 3
<211> LENGTH: 516
<212> TYPE: PRT
<213> ORGANISM: Homo sapiens

<400> SEQUENCE: 3
```

| | | | | | | | | | | | | | | | |
|---|---|---|---|---|---|---|---|---|---|---|---|---|---|---|---|
| Met | Ala | Gly | Ser | Leu | Thr | Gly | Leu | Leu | Leu | Gln | Ala | Val | Ser | Trp | |
| 1 | | | | 5 | | | | | 10 | | | | | 15 | |
| Ala | Ser | Gly | Ala | Arg | Pro | Cys | Ile | Pro | Lys | Ser | Phe | Gly | Tyr | Ser | Ser |
| | | | 20 | | | | | 25 | | | | | 30 | | |
| Val | Val | Cys | Val | Cys | Asn | Ala | Thr | Tyr | Cys | Asp | Ser | Phe | Asp | Pro | Pro |
| | | 35 | | | | | 40 | | | | | 45 | | | |
| Thr | Phe | Pro | Ala | Leu | Gly | Thr | Phe | Ser | Arg | Tyr | Glu | Ser | Thr | Arg | Ser |
| | 50 | | | | | 55 | | | | | 60 | | | | |
| Gly | Arg | Arg | Met | Glu | Leu | Ser | Met | Gly | Pro | Ile | Gln | Ala | Asn | His | Thr |
| 65 | | | | | 70 | | | | | 75 | | | | | 80 |
| Gly | Thr | Gly | Leu | Leu | Leu | Thr | Leu | Gln | Pro | Glu | Gln | Lys | Phe | Gln | Lys |
| | | | | 85 | | | | | 90 | | | | | 95 | |
| Val | Lys | Gly | Phe | Gly | Gly | Ala | Met | Thr | Asp | Ala | Ala | Ala | Leu | Asn | Ile |
| | | | 100 | | | | | 105 | | | | | 110 | | |
| Leu | Ala | Leu | Ser | Pro | Pro | Ala | Gln | Asn | Leu | Leu | Leu | Lys | Ser | Tyr | Phe |
| | | 115 | | | | | 120 | | | | | 125 | | | |
| Ser | Glu | Glu | Gly | Ile | Gly | Tyr | Asn | Ile | Ile | Arg | Val | Pro | Met | Ala | Ser |
| | 130 | | | | | 135 | | | | | 140 | | | | |
| Cys | Asp | Phe | Ser | Ile | Arg | Thr | Tyr | Thr | Tyr | Ala | Asp | Thr | Pro | Asp | Asp |
| 145 | | | | | 150 | | | | | 155 | | | | | 160 |
| Phe | Gln | Leu | His | Asn | Phe | Ser | Leu | Pro | Glu | Glu | Asp | Thr | Lys | Leu | Lys |
| | | | | 165 | | | | | 170 | | | | | 175 | |
| Ile | Pro | Leu | Ile | His | Arg | Ala | Leu | Gln | Leu | Ala | Gln | Arg | Pro | Val | Ser |
| | | | 180 | | | | | 185 | | | | | 190 | | |
| Leu | Leu | Ala | Ser | Pro | Trp | Thr | Ser | Pro | Thr | Trp | Leu | Lys | Thr | Asn | Gly |
| | | 195 | | | | | 200 | | | | | 205 | | | |
| Ala | Val | Asn | Gly | Lys | Gly | Ser | Leu | Lys | Gly | Gln | Pro | Gly | Asp | Ile | Tyr |
| | 210 | | | | | 215 | | | | | 220 | | | | |
| His | Gln | Thr | Trp | Ala | Arg | Tyr | Phe | Val | Lys | Phe | Leu | Asp | Ala | Tyr | Ala |
| 225 | | | | | 230 | | | | | 235 | | | | | 240 |
| Glu | His | Lys | Leu | Gln | Phe | Trp | Ala | Val | Thr | Ala | Glu | Asn | Glu | Pro | Ser |
| | | | | 245 | | | | | 250 | | | | | 255 | |
| Ala | Gly | Leu | Leu | Ser | Gly | Tyr | Pro | Phe | Gln | Cys | Leu | Gly | Phe | Thr | Pro |
| | | | 260 | | | | | 265 | | | | | 270 | | |
| Glu | His | Gln | Arg | Asp | Phe | Ile | Ala | Arg | Asp | Leu | Gly | Pro | Thr | Leu | Ala |
| | | 275 | | | | | 280 | | | | | 285 | | | |
| Asn | Ser | Thr | His | His | Asn | Val | Arg | Leu | Leu | Met | Leu | Asp | Asp | Gln | Arg |
| | 290 | | | | | 295 | | | | | 300 | | | | |
| Leu | Leu | Leu | Pro | His | Trp | Ala | Lys | Val | Val | Leu | Thr | Asp | Pro | Glu | Ala |
| 305 | | | | | 310 | | | | | 315 | | | | | 320 |
| Ala | Lys | Tyr | Val | His | Gly | Ile | Ala | Val | His | Trp | Tyr | Leu | Asp | Phe | Leu |
| | | | | 325 | | | | | 330 | | | | | 335 | |
| Ala | Pro | Ala | Lys | Ala | Thr | Leu | Gly | Glu | Thr | His | Arg | Leu | Phe | Pro | Asn |
| | | | 340 | | | | | 345 | | | | | 350 | | |
| Thr | Met | Leu | Phe | Ala | Ser | Glu | Ala | Cys | Val | Gly | Ser | Lys | Phe | Trp | Glu |
| | | 355 | | | | | 360 | | | | | 365 | | | |
| Gln | Ser | Val | Arg | Leu | Gly | Ser | Trp | Asp | Arg | Gly | Met | Gln | Tyr | Ser | His |
| | 370 | | | | | 375 | | | | | 380 | | | | |

```
Ser Ile Ile Thr Asn Leu Leu Tyr His Val Gly Trp Thr Asp Trp
385                 390                 395                 400

Asn Leu Ala Leu Asn Pro Glu Gly Pro Asn Trp Val Arg Asn Phe
            405                 410                 415

Val Asp Ser Pro Ile Ile Val Asp Ile Thr Lys Asp Thr Phe Tyr Lys
        420                 425                 430

Gln Pro Met Phe Tyr His Leu Gly His Phe Ser Lys Phe Ile Pro Glu
        435                 440                 445

Gly Ser Gln Arg Val Gly Leu Val Ala Ser Gln Lys Asn Asp Leu Asp
    450                 455                 460

Ala Val Ala Leu Met His Pro Asp Gly Ser Ala Val Val Val Leu
465                 470                 475                 480

Asn Arg Ser Ser Lys Asp Val Pro Leu Thr Ile Lys Asp Pro Ala Val
            485                 490                 495

Gly Phe Leu Glu Thr Ile Ser Pro Gly Tyr Ser Ile His Thr Tyr Leu
        500                 505                 510

Trp Arg Arg Gln
        515

<210> SEQ ID NO 4
<211> LENGTH: 1551
<212> TYPE: DNA
<213> ORGANISM: Homo sapiens

<400> SEQUENCE: 4
atggctggca gcctcacagg attgcttcta cttcaggcag tgtcgtgggc atcaggtgcc      60
cgcccctgca tccctaaaag cttcggctac agctcggtgg tgtgtgtctg caatgccaca     120
tactgtgact cctttgaccc ccgaccttt cctgccttg gtaccttcag ccgctatgag       180
agtacacgca gtgggcgacg gatggagctg agtatggggc ccatccaggc taatcacacg     240
ggcacaggcc tgctactgac cctgcagcca gaacagaagt tccagaaagt gaagggattt     300
ggaggggcca tgacagatgc tgctgctctc aacatccttg ccctgtcacc ccctgcccaa     360
aatttgctac ttaaatcgta cttctctgaa aaggaatcg atataacat catccgggta      420
cccatggcca gctgtgactt ctccatccgc acctacacct atgcagacac ccctgatgat     480
ttccagttgc acaacttcag cctcccagag aagatacca agctcaagat acccctgatt     540
caccgagccc tgcagttggc ccagcgtccc gtttcactcc ttgccagccc ctggacatca     600
cccacttggc tcaagaccaa tggagcggtg aatgggaagg ggtcactcaa gggacagccc     660
ggagacatct accaccagac ctgggccaga tactttgtga gttcctgga tgcctatgct      720
gagcacaagt tacagttctg ggcagtgaca gctgaaaatg agccttctgc tgggctgttg     780
agtggatacc ccttccagtg cctgggcttc accctgaac atcagcgaga cttcattgcc     840
cgtgacctag tcctaccct cgccaacagt actcaccaca atgtccgcct actcatgctg     900
gatgaccaac gcttgctgct gccccactgg gcaaaggtgg tactgacaga cccagaagca     960
gctaaatatg ttcatggcat tgctgtacat tggtacctgg actttctggc tccagccaaa    1020
gccaccctag gggagacaca ccgcctgttc cccaacacca tgctctttgc ctcagaggcc    1080
tgtgtgggct ccaagttctg ggagcagagt gtgcggctag ctcctgggga tcgagggatg    1140
cagtacagcc acagcatcat cacgaacctc ctgtaccatg tggtcggctg gaccgactgg    1200
aaccttgccc tgaaccccga aggaggacc aattgggtgc gtaactttgt cgacagtccc    1260
atcattgtag acatcaccaa ggacacgtt tacaaacagc ccatgttcta ccaccttggc    1320
```

-continued

```
cacttcagca agttcattcc tgagggctcc cagagagtgg ggctggttgc cagtcagaag    1380
aacgacctgg acgcagtggc actgatgcat cccgatggct ctgctgttgt ggtcgtgcta    1440
aaccgctcct ctaaggatgt gcctcttacc atcaaggatc ctgctgtggg cttcctggag    1500
acaatctcac ctggctactc cattcacacc tacctgtggc gtcgccagtg a             1551

<210> SEQ ID NO 5
<211> LENGTH: 36
<212> TYPE: DNA
<213> ORGANISM: Artificial Sequence
<220> FEATURE:
<223> OTHER INFORMATION: Forward primer

<400> SEQUENCE: 5
gcggaattcg ccaccatggc tggcagcctc acagga                               36

<210> SEQ ID NO 6
<211> LENGTH: 24
<212> TYPE: DNA
<213> ORGANISM: Artificial Sequence
<220> FEATURE:
<223> OTHER INFORMATION: Reverse primer

<400> SEQUENCE: 6
ctcgagtcac tggcgacgcc acag                                            24
```